(12) United States Patent
Waugh et al.

(10) Patent No.: US 7,807,780 B2
(45) Date of Patent: Oct. 5, 2010

(54) MULTI-COMPONENT BIOLOGICAL TRANSPORT SYSTEMS

(75) Inventors: Jacob Waugh, Millbrae, CA (US); Michael Dake, Stanford, CA (US)

(73) Assignee: Revance Therapeutics, Inc., Newark, CA (US)

( * ) Notice: Subject to any disclaimer, the term of this patent is extended or adjusted under 35 U.S.C. 154(b) by 0 days.

(21) Appl. No.: 09/910,432

(22) Filed: Jul. 20, 2001

(65) Prior Publication Data
US 2003/0229034 A1 Dec. 11, 2003

Related U.S. Application Data

(60) Provisional application No. 60/220,244, filed on Jul. 21, 2000.

(51) Int. Cl.
| | |
|---|---|
| *C07K 14/16* | (2006.01) |
| *C07K 16/18* | (2006.01) |
| *C07K 14/62* | (2006.01) |
| *C07K 14/575* | (2006.01) |
| *C07K 14/33* | (2006.01) |

(52) U.S. Cl. .............. 530/327; 424/78.02; 424/78.03; 424/78.07; 424/78.17; 424/134.1; 530/303; 530/350; 530/387.1

(58) Field of Classification Search .............. None
See application file for complete search history.

(56) References Cited

U.S. PATENT DOCUMENTS

| | | | |
|---|---|---|---|
| 4,434,228 A | 2/1984 | Swann | |
| 4,816,568 A | 3/1989 | Hamilton, Jr. et al. | |
| 5,252,713 A | 10/1993 | Morgan, Jr. et al. | |
| 5,420,105 A | 5/1995 | Gustavson et al. | |
| 5,512,547 A | 4/1996 | Johnson et al. | |
| 5,607,691 A | 3/1997 | Hale et al. | |
| 5,629,020 A | 5/1997 | Leone-Bay et al. | |
| 5,709,861 A | 1/1998 | Santiago et al. | |
| 5,744,166 A * | 4/1998 | Illum ..................... | 424/501 |
| 5,747,641 A | 5/1998 | Frankel et al. | |
| 5,756,468 A | 5/1998 | Johnson et al. | |
| 5,766,605 A | 6/1998 | Sanders et al. | |
| 5,795,587 A | 8/1998 | Gao et al. | |
| 5,804,604 A | 9/1998 | Frankel et al. | |
| 5,877,278 A | 3/1999 | Zuckermann et al. | |
| 5,985,434 A | 11/1999 | Qin et al. | |
| 5,989,545 A * | 11/1999 | Foster et al. ............. | 424/183.1 |
| 6,217,912 B1 | 4/2001 | Park et al. | |
| 6,280,937 B1 * | 8/2001 | Luo et al. .................. | 435/6 |
| 6,306,423 B1 | 10/2001 | Donovan et al. | |
| 6,312,708 B1 | 11/2001 | Donovan | |
| 6,383,509 B1 | 5/2002 | Donovan et al. | |
| 6,413,941 B1 | 7/2002 | Garnett et al. | |
| 6,495,663 B1 | 12/2002 | Rothbard et al. | |
| 6,506,399 B2 | 1/2003 | Donovan | |
| 6,511,676 B1 * | 1/2003 | Boulikas .................. | 424/450 |
| 6,585,993 B2 | 7/2003 | Donovan et al. | |
| 6,593,292 B1 | 7/2003 | Rothbard et al. | |
| 6,610,820 B1 | 8/2003 | Bonny | |
| 6,645,501 B2 | 11/2003 | Dowdy | |
| 6,669,951 B2 | 12/2003 | Rothbard et al. | |
| 6,670,322 B2 | 12/2003 | Goodnough et al. | |
| 6,680,301 B2 * | 1/2004 | Berg et al. ..................... | 514/44 |
| 6,683,049 B1 | 1/2004 | Aoki et al. | |
| 6,692,911 B2 | 2/2004 | Pack et al. | |
| 6,696,038 B1 | 2/2004 | Mahato et al. | |
| 6,730,293 B1 | 5/2004 | Rothbard et al. | |
| 6,759,387 B2 | 7/2004 | Rothbard et al. | |
| 6,831,059 B2 | 12/2004 | Donovan | |
| 6,866,856 B2 | 3/2005 | Lu et al. | |
| 6,896,886 B2 | 5/2005 | Aoki et al. | |
| 6,974,578 B1 | 12/2005 | Aoki et al. | |
| 7,008,924 B1 * | 3/2006 | Yan et al. ..................... | 514/12 |
| 7,056,656 B1 | 6/2006 | Rana et al. | |
| 7,060,498 B1 | 6/2006 | Wang | |
| 2001/0024716 A1 | 9/2001 | Chen et al. | |
| 2002/0009491 A1 | 1/2002 | Rothbard et al. | |
| 2002/0131965 A1 | 9/2002 | Rothbard et al. | |
| 2003/0022831 A1 | 1/2003 | Rothbard et al. | |
| 2003/0032593 A1 | 2/2003 | Wender et al. | |
| 2003/0086256 A1 | 5/2003 | Rothbard et al. | |
| 2003/0104622 A1 | 6/2003 | Robbins et al. | |
| 2003/0118598 A1 | 6/2003 | Hunt | |
| 2003/0138437 A1 | 7/2003 | Hunt | |
| 2003/0162719 A1 | 8/2003 | Rothbard et al. | |
| 2003/0165567 A1 | 9/2003 | Mixson | |
| 2003/0185788 A1 | 10/2003 | Rothbard et al. | |
| 2003/0215395 A1 | 11/2003 | Yu et al. | |
| 2003/0220480 A1 | 11/2003 | Bonny | |
| 2003/0229034 A1 | 12/2003 | Waugh et al. | |
| 2003/0236214 A1 * | 12/2003 | Wolff et al. ................... | 514/44 |
| 2004/0009180 A1 | 1/2004 | Donovan | |
| 2004/0009469 A1 | 1/2004 | Apt et al. | |
| 2004/0013687 A1 | 1/2004 | Simpson | |
| 2004/0033241 A1 | 2/2004 | Donovan | |

(Continued)

FOREIGN PATENT DOCUMENTS

EP 1180524 2/2002

(Continued)

OTHER PUBLICATIONS

Wu et al (J. Biol. Chem 262(10): 4429-4432, 1987).*

(Continued)

*Primary Examiner*—Richard Schnizer
(74) *Attorney, Agent, or Firm*—Kenneth H. Sonnenfeld; Joseph D. Eng, Jr.; King & Spalding LLP

(57) ABSTRACT

Compositions and methods are provided that are useful for the delivery of therapeutic agents, including nucleic acids. The compositions can be prepared with components useful for targeting the delivery of the compositions as well as imaging components.

6 Claims, 12 Drawing Sheets

U.S. PATENT DOCUMENTS

| | | | |
|---|---|---|---|
| 2004/0037853 | A1 | 2/2004 | Borodic |
| 2004/0127556 | A1 | 7/2004 | Lu et al. |
| 2004/0147443 | A1 | 7/2004 | Renault |
| 2004/0161405 | A9 | 8/2004 | Rothbard et al. |
| 2004/0186045 | A1 | 9/2004 | Rothbard et al. |
| 2004/0192754 | A1 | 9/2004 | Shapira et al. |
| 2004/0220100 | A1 | 11/2004 | Waugh et al. |
| 2004/0220386 | A1 | 11/2004 | Steward et al. |
| 2004/0247614 | A1 | 12/2004 | Dorr et al. |
| 2004/0247623 | A1 | 12/2004 | Cady |
| 2005/0074461 | A1 | 4/2005 | Donovan |
| 2005/0112146 | A1 | 5/2005 | Graham |
| 2005/0175636 | A1 | 8/2005 | Donovan |
| 2005/0196414 | A1 | 9/2005 | Dake et al. |
| 2005/0232966 | A1 | 10/2005 | Hughes et al. |
| 2005/0238667 | A1 | 10/2005 | Hunt |
| 2005/0239705 | A1 | 10/2005 | Dake et al. |
| 2006/0018931 | A1 | 1/2006 | Taylor |
| 2006/0024331 | A1 | 2/2006 | Fernandez-Salas |
| 2006/0040882 | A1 | 2/2006 | Chen |
| 2007/0077259 | A1 | 4/2007 | Dake et al. |

FOREIGN PATENT DOCUMENTS

| | | | |
|---|---|---|---|
| WO | WO 92/07871 | | 5/1992 |
| WO | WO 94/04686 | | 3/1994 |
| WO | WO 96/11712 | * | 4/1996 |
| WO | WO 97/40854 | | 11/1997 |
| WO | WO 98/19710 | | 5/1998 |
| WO | WO 98/22610 | | 5/1998 |
| WO | WO 98/24596 | | 5/1999 |
| WO | WO 99/24596 | * | 5/1999 |
| WO | WO 99/42901 | | 8/1999 |
| WO | WO 00/24419 | | 5/2000 |
| WO | WO 00 24419 | | 5/2000 |
| WO | WO 00/32764 | | 6/2000 |
| WO | WO 00/34308 | | 6/2000 |
| WO | WO 01/13957 | | 3/2001 |
| WO | WO 01/62297 | | 8/2001 |
| WO | WO 02 07773 | | 1/2002 |
| WO | WO 02/07773 | | 1/2002 |
| WO | WO 02/065986 | | 8/2002 |
| WO | WO 02/067917 | | 9/2002 |
| WO | WO 02/069930 | | 9/2002 |
| WO | WO 03/049772 | | 6/2003 |
| WO | WO 03 072049 | | 9/2003 |
| WO | WO 2006/005910 | | 1/2006 |

OTHER PUBLICATIONS

GenBank Accession No. M77788 (2005).*
Cristiano et al (Proc. Nat. Acad. Sci. USA 90: 11548-11552).*
Puls et al (Gene Therapy 6: 1774-1778, 1999).*
http://www.genlantis.com/catalog/product_line. cfm?product_family_key=13&product_line_key=54, retrieved from the internet on Sep. 2, 2005.*
1998 Promega Catalog, pp. 262-265.*
Kabanov et al (Adv. Drug Del. Rev 30: 49-610, 1998).*
Console et al., "Antennapedia and HIV Transcription (TAT) Promote Endocytosis of High Molecular Weight Cargo Upon Binding to Cell Surface Clycosaminoglycans", J. Biol. Chem. vol. 278, No. 37, pp. 35109-35114.
Crosland et al., "Detection of Sparse Botulinum Toxin A Binding Sites using Fluorescent Latex Microspheres", J. of Histotechnology, vol. 22, No. 2, pp. 113-115, Jun. 1999.
Schantz et al., "Properties and Use of Botulinum Toxin and Other Microbial Neurotoxins in Medicine". Microbiological Reviews, Col. 56, No. 1, Mar. 1992, pp. 80-89.
Schwartz et al., "Peptide-Mediated Cellular Delivery" Curr. Opin. Mol. Ther. vol. 2, No. 2 pp. 162-167, 2000.
Shalaby, "Polymers for Augmenting Botulinum Vaccine Efficiency"—Abstract.
Urbanova et al., "Noncovalent interaction of peptides with porphyrins in aqueous solution: conformational study using vibrational CD spectroscopy", Biopolymers (Peptide Science), col. 60, pp. 307-316, 2001.

1992 Sigma Catalog, p. 1745.

Green, M. "Mutational analysis of HIV-1 TAT minimal domain peptides: identification of trans-dominant mutants that suppress HIV-LTR-driven gene expression", Cell, 58:215-223.

"AIDS, Use of HIV-1 TAT, to target and/or activate antigen-presenting cells, and/or to deliver cargo molecules" from http://pharmalicensing.com/public/outlicensing/view/3766 (2001).

Printout of website for "botulinum cream" from http://www.ebigchina.com/ebcps/4/pd/82305.html.

http:www.genlantis.com/catalog/product_line.cfm?product_family_key=13&product_line_key=54, retrieved from the internet on Sep. 2, 2005.

U.S. Appl. No. 11/816,602, filed Aug. 17, 2007, Dake, et al.

U.S. Appl. No. 10/591,486, filed Jun. 18, 2007, Dake, et al.

U.S. Appl. No. 10/591,732, filed Sep. 1, 2006, Dake, et al.

U.S. Appl. No. 10/591,485, filed Sep. 1, 2006, Waugh et al.

U.S. Appl. No. 11/954,885, filed Dec. 12, 2007, Waugh, et al.

U.S. Appl. No. 11/955,076, filed Dec. 12, 2007, Waugh, et al.

Blanes-Mira et al., Identification of Snare complex Modulators that Inhibit Exocytosis from an Alpha-Helix-Constrained Combinatorial Library, *Biochem. J.*, vol. 375(1), pp. 159-166, Oct. 1, 2003.

Blanes-Mira et al., Small peptides after the N-Terminus domain of Snap25 Inhibit Snare complex assembly and regulated exocytosis, *J. of Neurochem.*, vol. 88(1), pp. 124-135, Jan. 2004.

Blanes-Mira et al., A Synthetic Hexapeptide Argireline) with Antiwrinkle Activity, *Int'l J. of Cosmetic Science*, vol. 24(5), pp. 303-310, 2002.

Fisher et al., Matrix Sialoprotein of Developing Bone, *J. Biol. Chem.*, vol. 258, pp. 12723-12727, Oct. 1983.

Voet et al., Biochemistry, Second Edition, John Wiley and Sons, Inc., pp. 1275-1276, 1995.

Kalderon et al. A Short Amino Acid Sequence Able to Specify Nuclear Location, Cell, vol. 39, pp. 499-509, 1984.

Lieber et al., "Adenoviral Preterminal Protein Stabilizes Mini-Adenoviral Genomes in Vitro and in Vivo," Nature Biotechnology, vol. 15, pp. 1383-1387. Dec. 15, 1997.

* cited by examiner

MULTI-COMPONENT BIOLOGICAL TRANSPORT SYSTEMS

CROSS-REFERENCES TO RELATED APPLICATIONS

This application claims priority to provisional application Ser. No. 60/220,244, filed Jul. 21, 2001, the contents of which are incorporated herein by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

Gene delivery systems can be broadly classified into two groups: viral and nonviral. Viral systems have major toxicity risks and have resulted in major complications and death in clinical trials. Nonviral systems are far less efficient than viral approaches but offer the potential to tailor applications to enhance specificity and potentially decrease toxicity. Nonviral strategies can be broadly classified as lipid-based or non-lipid-based. The strategy presented in this invention can be applied to any of the existing nonviral approaches, so all will be described here.

The simplest nonviral system is direct delivery of DNA. Due to the negative charge of DNA, very little of the DNA actually enters the cell and most is degraded. Virtually none of the DNA enters the nucleus without a nuclear targeting sequence in the strategy. Conventionally, another factor is employed to enhance the efficiency of gene/product delivery (DNA, RNA, or more recently protein therapeutics) either by mechanical effects such as electroporation, ultrasound, "gene gun" and direct microinjection, or by charge neutralization and chemical effects with agents such as calcium phosphate, polylysine, and liposome preparations. In the latter strategies, charge neutralization has been shown to increase nonspecific efficiencies several-fold over even chemical/mechanical effects of liposome preparations alone. Based upon these and similar results, many have concluded that DNA and RNA require charge neutralization for efficiency in cellular uptake, since DNA's negative charge essentially precludes transport except by endolysis with subsequent lysosome fusion (escaped with addition of other agents). Most transfection agents actually use an excess of positive charge in ratios of 2-4 fold over the net DNA negative charge. The resulting positive hybrid binds ionically to negatively-charged cell surface proteoglycans and dramatically enhances subsequent uptake. Some transfection agents seem to have a cellular tropism, most likely because of steric and charge patterns that more effectively target particular proteoglycans, which vary in cell-type specific patterns. Even with appropriate agents (i.e., correct tropism), charge neutralization alone or in combination with liposomes remains extremely inefficient relative to viral strategies. Thus, the community has identified a number of peptides and peptide fragments which facilitate efficient entry of a complex into a cell and past any endolysosome stage. Several such transport factors even allow efficient nuclear entry. In one process, the transport factor is directly linked to the therapeutic product of interest (small drug, gene, protein, etc). This approach requires that a new drug attached to the transport factor be produced, purified and tested. In many cases, these hybrids will actually constitute new drugs and will require full testing. Such a process results in significant additional risk and expense. Alternately, a number of strategies merely employ mixing of the agent nonspecifically (or even specifically at the surface) into liposome preparations as carriers for a drug/DNA/factor. Although an improvement over direct or simpler modalities in terms of efficiencies, these approaches remain inefficient (relative to virus) and considerably more toxic than simple nonviral strategies. Part of this inefficiency is due to poor nuclear translocation. As a result, strategies have evolved to add nuclear translocation signals to the complex detailed above, either as part of the therapeutic factor hybrid or as part of the liposome mixture. Additional refinements have included efforts to reduce DNA/RNA/factor degradation.

Perhaps the most important refinements in the basic strategies presented above have included specific ligands or other targeting agents together with the therapeutic factor. These strategies offer the potential for greatly reduced nonspecific toxicity and substantial improvements in efficiency, particularly when combined with efficiency agents described as above. However, the current strategies rely on covalent linkages to a single carrier and thus necessitate a specific synthesis (to assure that steric considerations in a degree of substitution scheme don't favor a single factor over the others—i.e., to assure that each efficiency factor and each imaging moiety, and each targeting moiety is present on the backbone). This renders virtually impossible a number of specific constructs (for example, sialyl-lewis X and an Fab fragment to a surface antigen, since steric limitations would prevent efficient binding of one or the other in most schemes, and in turn would interfere with efficiency factors). While promising in concept, these approaches represent expensive, very low yield (in terms of synthesis), and unproven solutions to this problem.

As must be evident, with each stage of development in nonviral gene and factor delivery, problems have been encountered and, in the next stage, solved with an added degree of complexity. Each improvement represented an incremental step over the prior standard. However, the added complexity brings risk from a patient-care standpoint and inefficiency and expense from a production standpoint. These barriers have led to greatly decreased enthusiasm for these otherwise promising potential therapies.

What is needed are new methods and compositions that are broadly applicable to compositions of diverse therapeutic or cosmoceutic agents, that can be targeted or imaged to maximize delivery to a particular site. Surprisingly, the present invention provides such compositions and methods.

SUMMARY OF THE INVENTION

In one aspect, the present invention provides a composition comprising a non-covalent association complex of:
   a) a positively-charged backbone; and
   b) at least two members selected from:
      i) a first negatively-charged backbone having a plurality of attached imaging moieties;
      ii) a second negatively-charged backbone having a plurality of attached targeting agents;
      iii) at least one member selected from RNA, DNA, ribozymes, modified oligonucleotides and cDNA encoding a selected transgene;
      iv) DNA encoding at least one persistence factor; and
      v) a third negatively-charged backbone having a plurality of attached biological agents;
   wherein the association complex carries a net positive charge and at least one of the two members from group b) is selected from groups i), iii) or v).

The biological agents, in this aspect of the invention, can be either a therapeutic agent or a cosmoceutic agent. Alternatively, candidate agents can be used to determine in vivo efficacy in these non-covalent association complexes.

In another aspect, the present invention provides a composition comprising a non-covalent association complex of a positively-charged backbone having at least one attached efficiency group and at least one nucleic acid member selected from the group consisting of RNA, DNA, ribozymes, modified oligonucleotides and cDNA encoding a selected transgene.

In another aspect, the present invention provides a method for delivery of a biological agent to a cell surface in a subject, said method comprising administering to said subject a composition as described above.

In yet another aspect, the present invention provides a method for preparing a pharmaceutical or cosmoceutical composition, the method comprising combining a positively charged backbone component and at least two members selected from:
  i) a negatively-charged backbone having a plurality of attached imaging moieties;
  ii) a negatively-charged backbone having a plurality of attached targeting agents;
  iii) at least member selected from RNA, DNA, ribozymes, modified oligonucleotides and cDNA encoding a selected transgene;
  iv) DNA encoding at least one persistence factor; and
  v) a negatively-charged backbone having a plurality of attached therapeutic or cosmoceutic agents;
  with a pharmaceutically or cosmoceutically acceptable carrier to form a non-covalent association complex having a net positive charge, with the proviso that at least one of said two members from groups i) through v) is selected from groups i), iii) or v).

In still another aspect, the present invention provides a kit for formulating a pharmaceutical or cosmoceutical delivery composition, the kit comprising a positively charged backbone component and at least two components selected from groups i) through v) above, along with instructions for preparing the delivery composition.

DESCRIPTION OF THE INVENTION

General

Figure 1:
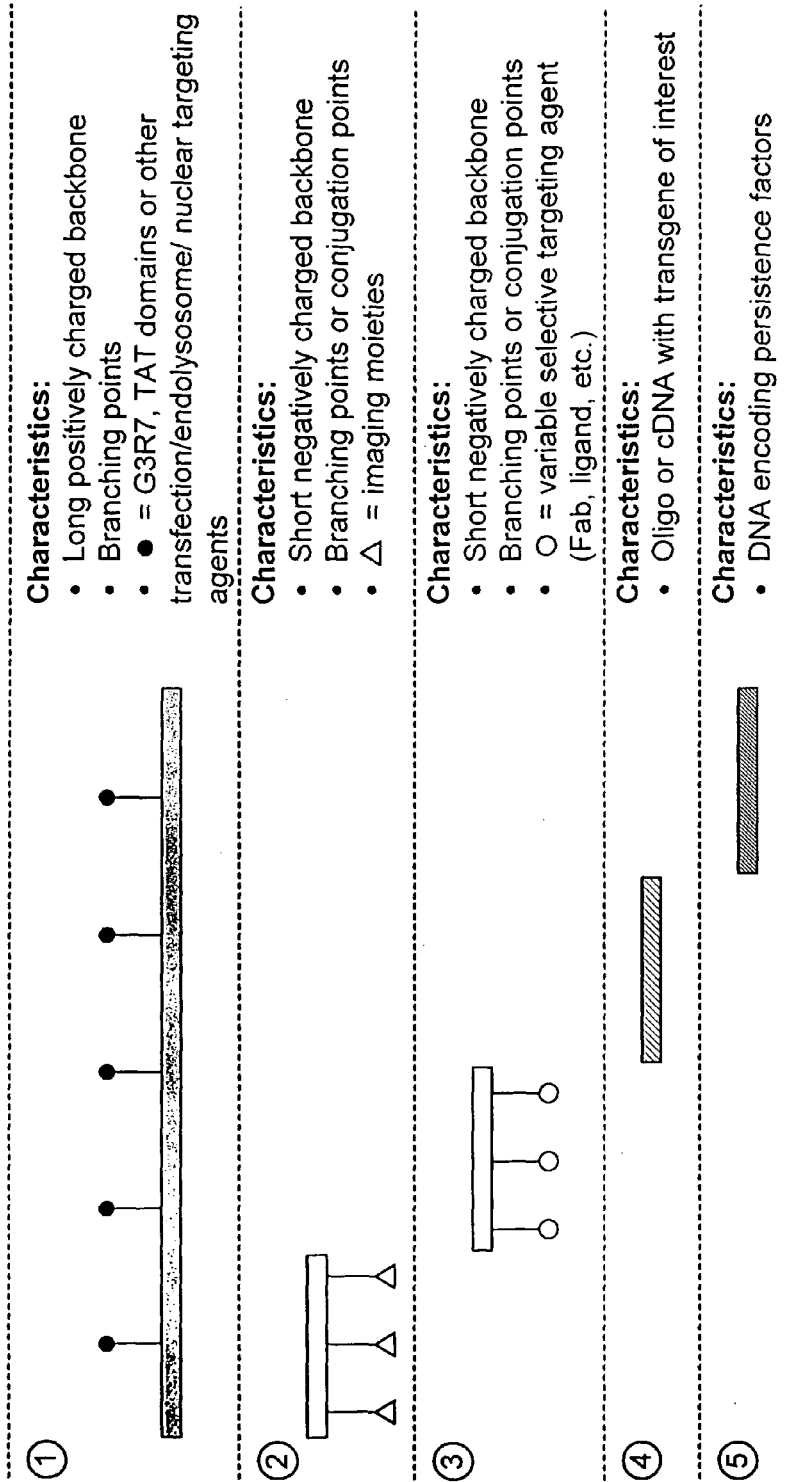
FIG. 1 provides a schematic representation the components used in the invention (G3R7=SEQ ID NO:1).
Figure 2:
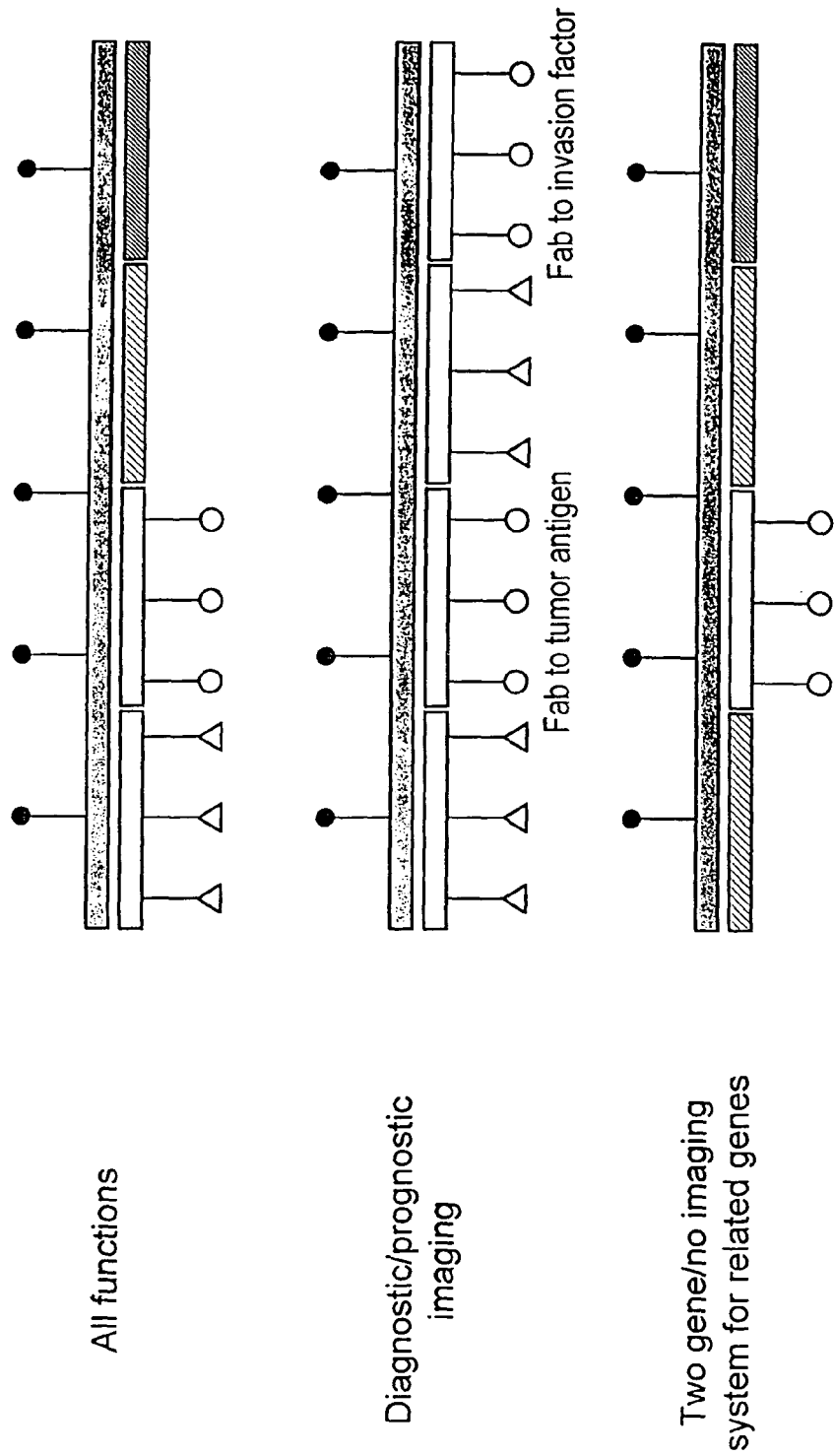
FIG. 2 provides a schematic representation of several embodiments of the invention.
Figure 3:
FIGS. 3-10 provide photographs depicting transdermal delivery of a therapeutic formulation as described in Example 4.
Figure 4:
Figure 5:
Figure 6:
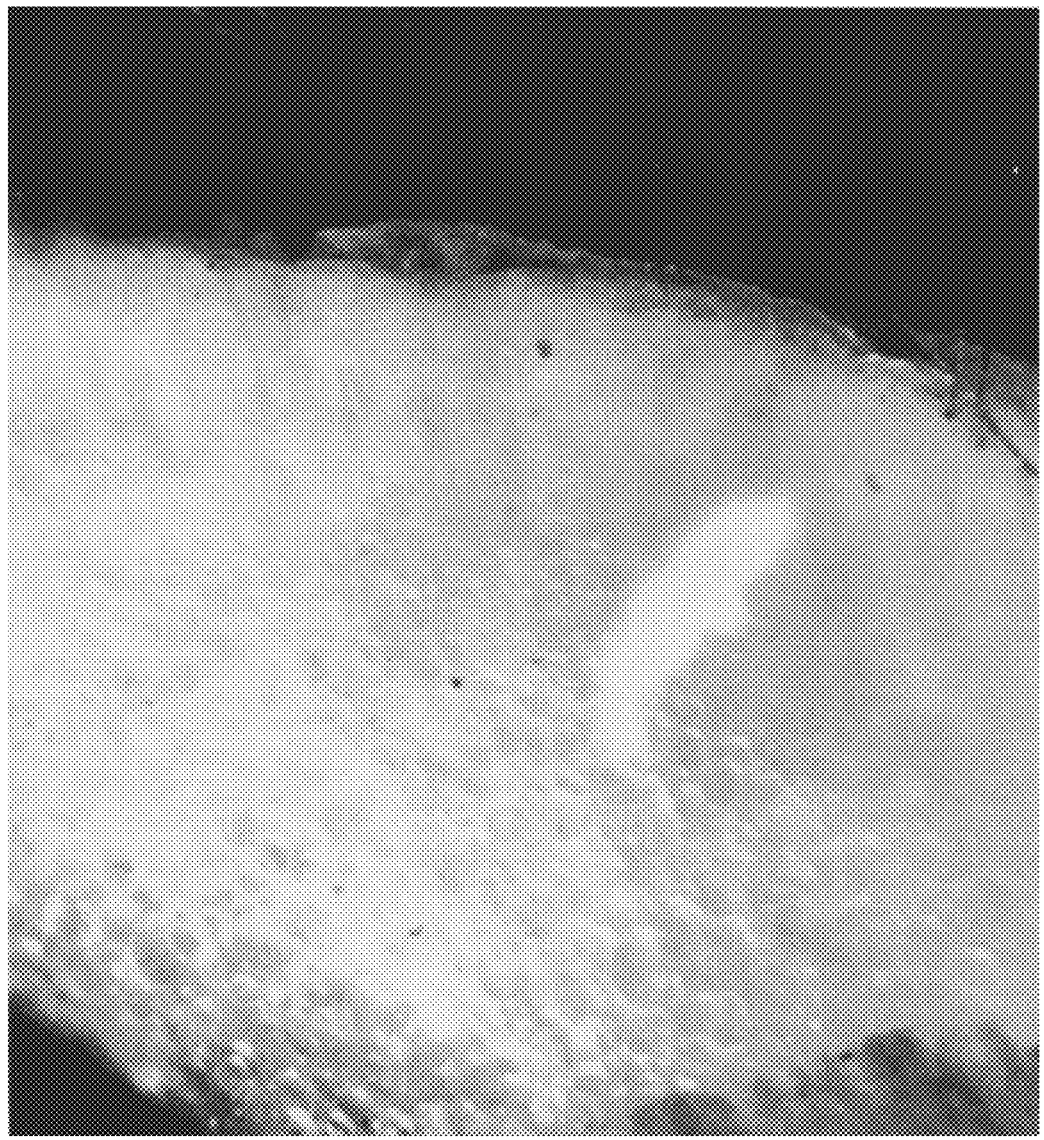

The present invention provides a component-based system for selective, persistent, delivery of imaging agents, genes or other therapeutic agents. Individual features for the compositions can be selected by designating desired components in bedside formulations. Additionally, imaging and specific targeting moieties are provided on separate negatively charged backbones which will form a non-covalent ionic association with a positive backbone. By placing these components on a negatively charged backbone, the invention obviates the need for attaching components in precise locations on a positive backbone as employed in other strategies (increasing complexity and expense and decreasing efficiency to a level that no successful combination has yet been reported due to steric limitations). Further understanding of the invention is provided with reference to FIG. 1. In this figure, the components are shown as (1) a solid backbone having attached positively charged groups (also referred to as efficiency groups shown as darkened circles attached to a darkened bar), for example $(Gly)_{n1}$-$(Arg)_{n2}$ (SEQ ID NOS:2-7) (wherein the subscript n1 is an integer of from 3 to about 5, and the subscript n2 is an odd integer of from about 7 to about 17) or TAT domains; (2) a short negatively charged backbone having attached imaging moieties (open triangles attached to a light bar); (3) a short negatively charged backbone having attached targeting agents and/or therapeutic agents (open circles attached to a light bar); (4) an oligonucleotide, RNA, DNA or cDNA (light cross hatched bar); and (5) DNA encoding persistence factors (dark cross hatched bar). FIG. 2 illustrates various examples of multicomponent compositions wherein the groups are depicted as set out in FIG. 1. For example, in FIG. 2, a first multi-component composition is illustrated in which a positively charged backbone has associated an imaging component, a targeting component, an oligonucleotide and a persistence factor. A second multi-component composition is illustrated which is designed for diagnostic/prognostic imaging. In this composition the positively charged backbone is complexed with both imaging components and targeting components. Finally, a third multi-component system is illustrated which is useful for gene delivery. In this system, an association complex is formed between a positively charged backbone, a targeting component, a gene of interest and DNA encoding a persistence factor. The present invention, described more fully below, provides a number of additional compositions useful in therapeutic and diagnostic programs.

Description of the Embodiments

Compositions

In view of the above, the present invention provides in one aspect a composition comprising a non-covalent association complex of:
  a) a positively-charged backbone; and
  b) at least two members selected from:
    i) a first negatively-charged backbone having a plurality of attached imaging moieties;
    ii) a second negatively-charged backbone having a plurality of attached targeting agents;
    iii) at least one member selected from RNA, DNA, ribozymes, modified oligonucleotides and cDNA encoding a selected transgene;
    iv) DNA encoding at least one persistence factor; and
    v) a third negatively-charged backbone having a plurality of attached biological agents;
  wherein the association complex carries a net positive charge and at least one of the two members from group b) is selected from groups i), iii) or v).

In one group of embodiments, the composition comprises at least three members selected from groups i) through v). In another group of embodiments, the composition comprises at least one member from each of groups i), ii), iii) and iv). In yet another group of embodiments, the composition comprises at least one member from each of groups i) and ii). And in another group of embodiments, the composition comprises at least one member from each of groups ii), iii) and iv).

Preferably, the positively-charged backbone has a length of from about 1 to 4 times the combined lengths of the members from group b). Alternatively, the positively charged backbone has a charge ratio of from about 1 to 4 times the combined charge of the members from group b). In some embodiments, the charge density is uniform and the length and charge ratios are approximately the same. Size to size (length) ratios can be determined based on molecular studies of the components or can be determined from the masses of the components.

Positively Charged Backbone

The positively-charged backbone is typically a linear chain of atoms, either with groups in the chain carrying a positive charge at physiological pH, or with groups carrying a positive charge attached to side chains extending from the backbone. The linear backbone is a hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), and the like). In one group of embodiments, the positively charged backbone is a polypropyleneamine wherein a number of the amine nitrogen atoms are present as ammonium groups (tetra-substituted) carrying a positive charge. In another group of embodiments, the backbone has attached a plurality of sidechain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups.

In one group of embodiments, the positively charged backbone is a polypeptide having multiple positively charged sidechain groups (e.g., lysine, arginine, ornithine, homoarginine, and the like). One of skill in the art will appreciate that when amino acids are used in this portion of the invention, the sidechains can have either the D- or L-form (R or S configuration) at the center of attachment.

Alternatively, the backbone can be an analog of a polypeptide such as a peptoid. See, for example, Kessler, *Angew. Chem. Int. Ed. Engl.* 32:543 (1993); Zuckermann et al. *Chemtracts-Macromol. Chem.* 4:80 (1992); and Simon et al. *Proc. Nat'l. Acad. Sci. USA* 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278. As the term is used herein, positively charged backbones that have a peptoid backbone construction are considered "non-peptide" as they are not composed of amino acids having naturally occurring sidechains at the α-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) *Chem. Rev.* 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

In a particularly preferred embodiment, the positively charged backbone is a polypeptide having branching groups (also referred to as efficiency groups) comprising -(gly)$_{n1}$-(arg)$_{n2}$ (SEQ ID NOS:8-18), HIV-TAT or fragments thereof, in which the subscript n1 is an integer of from 0 to 20, more preferably 0 to 8, still more preferably 2 to 5, and the subscript n2 is an odd integer of from about 5 to about 25, more preferably about 7 to about 17, most preferably about 7 to about 13. Still further preferred are those embodiments in which the HIV-TAT fragment has the formula (gly)$_p$-RGRD-DRRQRRR-(gly)$_q$ (SEQ ID NO:19) or (gly)$_p$-YGRKKRRQRRR-(gly)$_q$ (SEQ ID NO:20) wherein the subscripts p and q are each independently an integer of from 0 to 20 and the fragment is attached to the backbone via either the C-terminus or the N-terminus of the fragment. Preferred HIV-TAT fragments are those in which the subscripts p and q are each independently integers of from 0 to 8, more preferably 2 to 5.

In another particularly preferred embodiment, the backbone portion is a polylysine and positively charged branching groups are attached to the lysine sidechain amino groups. The polylysine used in this particularly preferred embodiment can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The appropriate selection of a polylysine will depend on the remaining components of the composition and will be sufficient to provide an overall net positive charge to the composition and provide a length that is preferably from one to four times the combined length of the negatively charged components. Preferred positively charged branching groups or efficiency groups include, for example, -gly-gly-gly-arg-arg-arg-arg-arg-arg-arg (-Gly$_3$Arg$_7$) (SEQ ID NO:1) or HIV-TAT.

Other Components

In addition to the positively charged backbone component, the compositions of the present invention comprise at least two components from the following:

i) a negatively-charged backbone having a plurality of attached imaging moieties;
 ii) a negatively-charged backbone having a plurality of attached targeting moieties;
 iii) at least one RNA, DNA, ribozyme, modified oligonucleotide or a cDNA encoding a transgene of interest;
 iv) DNA encoding at least one persistence factor; and v) a negatively-charged backbone having a plurality of attached therapeutic agents.

The negatively-charged backbones used to carry the imaging moieties, targeting moieties and therapeutic agents can be a variety of backbones (similar to those described above) having multiple groups carrying a negative charge at physiological pH. Suitable negatively-charged groups are carboxylic acids, phosphinic, phosphonic or phosphoric acids, sulfinic or sulfonic acids, and the like. In some embodiments, the negatively-charged backbone will be an oligonucleic acid. In other embodiments, the negatively-charged backbone is an oligosaccharide (e.g., dextran). In still other embodiments, the negatively-charged backbone is a polypeptide (e.g., poly glutamic acid, poly aspartic acid, or a polypeptide in which glutamic acid or aspartic acid residues are interrupted by uncharged amino acids). The moieties described in more detail below (imaging moieties, targeting agents, and therapeutic agents) can be attached to a backbone having these pendent groups, typically via ester linkages. Alternatively, amino acids which interrupt negatively-charged amino acids or are appended to the terminus of the negatively-charged backbone, can be used to attach imaging moieties and targeting moieties via, for example, disulfide linkages (through a cysteine residue), amide linkages, ether linkages (through serine or threonine hydroxyl groups) and the like.

Imaging Moieties

A variety of diagnostic or imaging moieties are useful in the present invention and are present in an effective amount that will depend on the condition being diagnosed or imaged, the route of administration, the sensitivity of the agent and device used for detection of the agent, and the like.

Examples of suitable imaging or diagnostic agents include radiopaque contrast agents, paramagnetic contrast agents, superparamagnetic contrast agents, CT contrast agents and other contrast agents. For example, radiopaque contrast agents (for X-ray imaging) will include inorganic and organic iodine compounds (e.g., diatrizoate), radiopaque metals and their salts (e.g., silver, gold, platinum and the like) and other radiopaque compounds (e.g., calcium salts, barium salts such as barium sulfate, tantalum and tantalum oxide). Suitable paramagnetic contrast agents (for MR imaging) include gadolinium diethylene triaminepentaacetic acid (Gd-DTPA) and its derivatives, and other gadolinium, manganese, iron, dysprosium, copper, europium, erbium, chromium, nickel and cobalt complexes, including complexes with 1,4,7,10-tetraazacyclododecane-N,N',N'',N'''-tetraacetic acid (DOTA), ethylenediaminetetraacetic acid (EDTA), 1,4,7,10-tetraazacyclododecane-N,N',N''-triacetic acid (DO3A), 1,4,7-triazacyclononane-N,N',N''-triacetic acid (NOTA), 1,4,8,10-tetraazacyclotetradecane-N,N',N'',N'''-tetraacetic acid (TETA), hydroxybenzylethylene-diamine diacetic acid (HBED) and the like. Suitable superparamagnetic contrast agents (for MR imaging) include magnetites, superparamagnetic iron oxides, monocrystalline iron oxides, particularly complexed forms of each of these agents that can be attached to a negatively charged backbone. Still other suitable imaging agents are the CT contrast agents including iodinated and noniodinated and ionic and nonionic CT contrast agents, as well as contrast agents such as spin-labels or other diagnostically effective agents.

Other examples of diagnostic agents include marker genes that encode proteins that are readily detectable when expressed in a cell, including, but not limited to, β-galactosidase, green fluorescent protein, blue fluorescent protein, luciferase, and the like. A wide variety of labels may be employed, such as radionuclides, fluors, enzymes, enzyme substrates, enzyme cofactors, enzyme inhibitors, ligands (particularly haptens), and the like. Still other useful substances are those labeled with radioactive species or components, such as $^{99}$mTc glucoheptonate.

Targeting Agents

A variety of targeting agents are useful in the compositions described herein. Typically, the targeting agents are attached to a negatively-charged backbone as described for the imaging moieties above. The targeting agents can be any element that makes it possible to direct the transfer of a nucleic acid, therapeutic agent or another component of the composition to a particular site. The targeting agent can be an extracellular targeting agent, which allows, for example, a nucleic acid transfer to be directed towards certain types of cells or certain desired tissues (tumor cells, liver cells, hematopoietic cells, and the like). Such an agent can also be an intracellular targeting agent, allowing a therapeutic agent to be directed towards particular cell compartments (e.g, mitochondria, nucleus, and the like).

The targeting agent or agents are preferably linked, covalently or non-covalently, to a negatively-charged backbone according to the invention. According to a preferred mode of the invention, the targeting agent is covalently attached to an oligonucleotide that serves as a negatively-charged backbone component, preferably via a linking group. Methods of attaching targeting agents (as well as other biological agents) to nucleic acids are well known to those of skill in the art using, for example, heterobifunctional linking groups (see Pierce Chemical Catalog). In one group of embodiments, the targeting agent is a fusogenic peptide for promoting cellular transfection, that is to say for favoring the passage of the composition or its various elements across membranes, or for helping in the egress from endosomes or for crossing the nuclear membrane. The targeting agent can also be a cell receptor ligand for a receptor that is present at the surface of the cell type, such as, for example, a sugar, transferrin, insulin or asialo-orosomucoid protein. Such a ligand may also be one of intracellular type, such as a nuclear location signal (nls) sequence which promotes the accumulation of transfected DNA within the nucleus.

Other targeting agents useful in the context of the invention, include sugars, peptides, hormones, vitamins, cytokines, oligonucleotides, lipids or sequences or fractions derived from these elements and which allow specific binding with their corresponding receptors. Preferably, the targeting agents are sugars and/or peptides such as antibodies or antibody fragments, cell receptor ligands or fragments thereof, receptors or receptor fragments, and the like. More preferably, the targeting agents are ligands of growth factor receptors, of cytokine receptors, or of cell lectin receptors or of adhesion protein receptors. The targeting agent can also be a sugar which makes it possible to target lectins such as the asialoglycoprotein receptors, or alternatively an antibody Fab fragment which makes it possible to target the Fc fragment receptor of immunoglobulins.

Nucleic Acids

In the compositions of the present invention, the nucleic acid can be either a deoxyribonucleic acid or a ribonucleic acid, and can comprise sequences of natural or artificial origin. More particularly, the nucleic acids used herein can include genomic DNA, cDNA, mRNA, tRNA, rRNA, hybrid sequences or synthetic or semi-synthetic sequences. These nucleic acids can be of human, animal, plant, bacterial, viral, etc. origin. Additionally, the nucleic acids can be obtained by any technique known to those skilled in the art, and in particular by the screening of banks, by chemical synthesis or by mixed methods including the chemical or enzymatic modification of sequences obtained by the screening of banks. Still further, the nucleic acids can be incorporated into vectors, such as plasmid vectors.

The deoxyribonucleic acids used in the present invention can be single- or double-stranded. These deoxyribonucleic acids can also code for therapeutic genes, sequences for regulating transcription or replication, antisense sequences, regions for binding to other cell components, etc. Suitable therapeutic genes are essentially any gene which codes for a protein product having a therapeutic effect. The protein product thus encoded may be a protein, polypeptide, a peptide, or the like. The protein product can, in some instances, be homologous with respect to the target cell (that is to say a product which is normally expressed in the target cell when the latter exhibits no pathology). In this manner, the use of suitable nucleic acids can increase the expression of a protein, making it possible, for example, to overcome an insufficient expression in the cell. Alternatively, the present invention provides compositions and methods for the expression of a protein which is inactive or weakly active due to a modification, or alternatively of overexpressing the protein. The therapeutic gene may thus code for a mutant of a cell protein, having increased stability, modified activity, etc. The protein product may also be heterologous with respect to the target cell. In this case, an expressed protein may, for example, make up or provide an activity which is deficient in the cell, enabling it to combat a pathology or to stimulate an immune response.

More particularly, nucleic acids useful in the present invention are those that code for enzymes, blood derivatives, hormones, lymphokines, interleukins, interferons, TNF, growth factors, neurotransmitters or their precursors or synthetic enzymes, or trophic factors: BDNF, CNTF, NGF, IGF, GMF, aFGF, bFGF, VEGF, NT3, NT5, HARP/pleiotrophin; the proteins involved in the metabolism of lipids, of apolipoprotein-types selected from apolipoproteins A-I, A-II, A-IV, B, C-I, C-II, C-III, D, E, F, G, H, J and apo(a), metabolic enzymes such as, for example, lipoprotein lipase, hepatic lipase, lecithin cholesterol acyltransferase, 7-α-cholesterol hydroxylase, phosphatidic acid phosphatase, or lipid transfer proteins such as cholesterol ester transfer protein and phospholipid transfer protein, a protein for binding HDLs or a receptor selected from, for example, LDL receptors, chylomicron-remnant receptors and scavenger receptors, dystrophin or minidystrophin, GAX protein, CFTR protein associated with mucoviscidosis, tumor-suppressant genes: p53, Rb, Rap1A, DCC, k-rev; protein factors involved in coagulation: factors VII, VIII, IX; or the nucleic acids can be those genes involved in DNA repair, suicide genes (thymidine kinase, cytosine deaminase), genes encoding thrombomodulin, α1-antitrypsin, tissue plasminogen activator, superoxide dismutase, elastase, matrix metalloproteinase, and the like.

The therapeutic genes useful in the present invention can also be an antisense sequence or a gene whose expression in the target cell makes it possible to control the expression of genes or the transcription of cellular mRNA. Such sequences can, for example, be transcribed in the target cell into complementary RNA of cellular mRNA and thus block their translation into protein, according to the technique described in patent EP 140,308. The antisense sequences also comprise the sequences coding for ribozymes which are capable of selectively destroying target RNA (see EP 321,201).

As indicated above, the nucleic acid may also contain one or more genes coding for an antigenic peptide, capable of generating an immune response in humans or animals. In this particular embodiment, the invention thus makes it possible to produce either vaccines or immunotherapeutic treatments applied to humans or to animals, in particular against microorganisms, viruses or cancers. They may in particular be antigenic peptides specific for Epstein Barr virus, for HIV virus, for hepatitis B virus (see EP 185,573), for pseudo-rabies virus or alternatively specific for tumors (see EP 259,212).

Preferably, the nucleic acid also comprises sequences that allow the expression of the therapeutic gene and/or of the gene coding for the antigenic peptide in the desired cell or organ. These can be sequences that are naturally responsible for expression of the gene considered when these sequences are capable of functioning in the infected cell. The nucleic acids can also be sequences of different origin (responsible for the expression of other proteins, or even synthetic proteins). In particular, the nucleic acids can contain promoter sequences for eukaryotic or viral genes. For example, the promoter sequences can be those derived from the genome of the cell which it is desired to infect. Similarly, the promoter sequences can be derived from the genome of a virus, e.g., the promoters of genes E1A, MLP, CMV, RSV, etc. In addition, these expression sequences may be modified by addition of activation sequences, regulation sequences, etc.

Moreover, the nucleic acid may also contain, in particular upstream of the therapeutic gene, a signal sequence which directs the therapeutic product synthesized into the secretion pathways of the target cell. This signal sequence may be the natural signal sequence of the therapeutic product, but it may also be any other functional signal sequence, or an artificial signal sequence.

DNA Encoding at Least One Persistence Factor

In some embodiments, the composition will also comprise DNA encoding at least one persistence factor. Exemplary of such DNA is the DNA encoding adenoviral preterminal protein 1 (see, Lieber, et al. *Nature Biotechnology* 15(13):1383-1387 (1997).

Biological Agents

A variety of biological agents, including both therapeutic and cosmoceutic agents, are useful in the present invention and are present in an effective amount that will depend on the condition being treated, prophylactically or otherwise, the route of administration, the efficacy of the agent and patient's size and susceptibility to the treatment regimen.

Suitable therapeutic agents that can be attached to a negatively charged backbone can be found in essentially any class of agents, including, for example, analgesic agents, anti-asthmatic agents, antibiotics, antidepressant agents, anti-diabetic agents, antifungal agents, antiemetics, antihypertensives, anti-impotence agents, anti-inflammatory agents, antineoplastic agents, anti-HIV agents, antiviral agents, anxiolytic agents, contraception agents, fertility agents, antithrombotic agents, prothrombotic agents, hormones, vaccines, immunosuppressive agents, vitamins and the like.

Suitable cosmeceutic agents include, for example, epidermal growth factor (EGF), as well as human growth hormone, antioxidants, and BOTOX.

More particularly, therapeutic agents useful in the present invention include such analgesics as lidocaine, novacaine, bupivacaine, procaine, tetracaine, benzocaine, cocaine, mepivacaine, etidocaine, proparacaine ropivacaine, prilocaine and the like; anti-asthmatic agents such as azelastine, ketotifen, traxanox, corticosteroids, cromolyn, nedocromil, albuterol, bitolterol mesylate, pirbuterol, salmeterol, terbutyline, theophylline and the like; antibiotic agents such as neomycin, streptomycin, chloramphenicol, norfloxacin, ciprofloxacin, trimethoprim, sulfamethyloxazole, the β-lactam antibiotics, tetracycline, and the like; antidepressant agents such as nefopam, oxypertine, imipramine, trazadone and the like; antidiabetic agents such as biguanidines, sulfonylureas, and the like; antiemetics and antipsychotics such as chloropromazine, fluphenazine, perphenazine, proclorperazine, promethazine, thiethylperazine, triflupromazine, haloperidol, scopolamine, diphenidol, trimethobenzamide, and the like; neuromuscular agents such as atracurium mivacurium, rocuronium, succinylcholine, doxacurium, tubocurarine, and botulinum toxin (BOTOX); antifungal agents such as amphotericin B, nystatin, candicidin, itraconazole, ketoconazole, miconazole, clotrimazole, fluconazole, ciclopirox, econazole, naftifine, terbinafine, griseofulvin and the like; antihypertensive agents such as propanolol, propafenone, oxyprenolol, nifedipine, reserpine and the like; anti-impotence agents such as nitric oxide donors and the like; anti-inflammatory agents including steroidal anti-inflammatory agents such as cortisone, hydrocortisone, dexamethasone, prednisolone, prednisone, fluazacort, and the like, as well as non-steroidal anti-inflammatory agents such as indomethacin, ibuprofen, ramifenizone, prioxicam and the like; antineoplastic agents such as adriamycin, cyclophosphamide, actinomycin, bleomycin, duanorubicin, doxorubicin, epirubicin, mitomycin, rapamycin, methotrexate, fluorouracil, carboplatin, carmustine (BCNU), cisplatin, etoposide, interferons, phenesterine, taxol (including analogs and derivatives), camptothecin and derivatives thereof, vinblastine, vincristine and the like; anti-HIV agents (e.g., antiproteolytics); antiviral agents such as amantadine, methisazone, idoxuridine, cytarabine, acyclovir, famciclovir, ganciclovir, foscamet, sorivudine, trifluridine, valacyclovir, cidofovir, didanosine, stavudine, zalcitabine, zidovudine, ribavirin, rimantatine and the like; anxiolytic agents such as dantrolene, diazepam and the like; COX-2 inhibitors; contraception agents such as progestogen and the like; anti-thrombotic agents such as GPIIb/IIIa inhibitors, tissue plasminogen activators, streptokinase, urokinase, heparin and the like; prothrombotic agents such as thrombin, factors V, VII, VIII and the like; hormones such as insulin, growth hormone, prolactin, EGF (epidermal growth factor) and the like; immunosuppressive agents such as cyclosporine, azathioprine, mizorobine, FK506, prednisone and the like; angiogenic agents such as VEGF (vascular endothelial growth factor); vitamins such as A, D, E, K and the like; and other therapeutically or medicinally active agents. See, for example, GOODMAN & GILMAN'S THE PHARMACOLOGICAL BASIS OF THERAPEUTICS, Ninth Ed. Hardman, et al., eds. McGraw-Hill, (1996).

In the most preferred embodiments, the biological agent is selected from insulin, botulinum toxin (BOTOX), VEGF, EGF, antibodies to VEGF, and TGF-β1.

Negatively-charged Backbones Having Attached Imaging Moieties Targeting Agents or Therapeutic Agents For three of the above groups of components (imaging moieties, targeting agents and therapeutic agents), the individual compounds are attached to a negatively charged backbone. Typically, the attachment is via a linking group used to covalently attach the particular agent to the backbone through functional groups present on the agent as well as the backbone. A variety of linking groups are useful in this aspect of the invention. See, for example, Hermanson, *Bioconjugate Techniques*, Academic Press, San Diego, Calif. (1996); Wong, S. S., Ed., *Chemistry of Protein Conjugation and Cross-Linking*, CRC Press, Inc., Boca Raton, Fla. (1991); Senter, et al., *J. Org. Chem.* 55:2975-78 (1990); and Koneko, et al., *Bioconjugate Chem.* 2:133-141 (1991).

In some embodiments, the therapeutic, diagnostic or targeting agents will not have an available functional group for attaching to a linking group, \ can be first modified to incorporate, for example, a hydroxy, amino, or thiol substituent. Preferably, the substituent is provided in a non-interfering portion of the agent, and can be used to attach a linking group, and will not adversely affect the function of the agent.

In yet another aspect, the present invention provides compositions comprising a non-covalent association complex of a positively-charged backbone having at least one attached efficiency group and at least one nucleic acid member selected from the group consisting of RNA, DNA, ribozymes, modified oligonucleotides and cDNA encoding a selected transgene. In this aspect of the invention, the positively-charged backbone can be essentially any of the positively-charged backbones described above, and will also comprise (as with selected backbones above) at least one attached efficiency group. Suitable efficiency groups include, for example, $(Gly)_{n1}-(Arg)_{n2}$ (wherein the subscript n1 is an integer of from 3 to about 5, and the subscript n2 is an odd integer of from about 7 to about 17) or TAT domains. Additionally, the nucleic acids useful in this aspect of the invention are the same as have been described above.

Methods of Preparing the Compositions

In another aspect, the present invention provides a method for preparing a pharmaceutical composition, the method comprising combining a positively charged backbone component and at least two members selected from:
 i) a first negatively-charged backbone having a plurality of attached imaging moieties;
 ii) a second negatively-charged backbone having a plurality of attached targeting agents;
 iii) at least one member selected from the group consisting of RNA, DNA, ribozymes, modified oligonucleotides and cDNA encoding a selected transgene;
 iv) DNA encoding at least one persistence factor; and
 v) a third negatively-charged backbone having a plurality of attached therapeutic agents;
 with a pharmaceutically acceptable carrier to form a non-covalent association complex having a net positive charge, with the proviso that at least one of the two members from groups i) through v) is selected from groups i), iii) or v).

The broad applicability of the present invention is illustrated by the ease with which a variety of pharmaceutical compositions can be formulated. Typically, the compositions are prepared by mixing the positively charged backbone component with the desired components of interest (e.g., DNA, targeting, imaging or therapeutic components) in ratios and a sequence to obtain compositions having a variable net positive charge. In many embodiments, the compositions can be prepared, for example, at bedside using pharmaceutically acceptable carriers and diluents for administration of the composition. Alternatively, the compositions can be prepared by suitable mixing of the components and then lyophilized and stored (typically at room temperature or below) until used or formulated into a suitable delivery vehicle.

The compositions can be formulated to provide mixtures suitable for topical, cutaneous, oral, rectal, vaginal, parenteral, intranasal, intravenous, intramuscular, subcutaneous, intraocular, transdermal, etc. administration. The pharmaceutical compositions of the invention preferably contain a vehicle which is pharmaceutically acceptable for an injectable formulation, in particular for direct injection into the desired organ, or for topical administration (to skin and/or mucous membrane). They may in particular be sterile, isotonic solutions or dry compositions, in particular freeze-dried compositions, which, by addition, depending on the case, of sterilized water or of physiological saline, allow injectable solutions to be made up. For example, the doses of nucleic acid used for the injection and the number of administrations may be adapted according to various parameters, and in particular according to the mode of administration used, the pathology concerned, the gene to be expressed, or alternatively the desired duration of the treatment.

Methods of Using the Compositions

Delivery Methods

The compositions of the present invention can be delivered to a subject, cell or target site, either in vivo or ex vivo using a variety of methods. In fact, any of the routes normally used for introducing a composition into ultimate contact with the tissue to be treated can be used. Preferably, the compositions will be administered with pharmaceutically acceptable carriers. Suitable methods of administering such compounds are available and well known to those of skill in the art, and, although more than one route can be used to administer a particular composition, a particular route can often provide a more immediate and more effective reaction than another route. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17$^{th}$ ed. 1985).

Administration can be, for example, intravenous, topical, intraperitoneal, subdermal, subcutaneous, transcutaneous, intramuscular, oral, intra-joint, parenteral, intranasal, or by inhalation. Suitable sites of administration thus include, but are not limited to, the skin, bronchium, gastrointestinal tract, eye and ear. The compositions typically include a conventional pharmaceutical carrier or excipient and can additionally include other medicinal agents, carriers, adjuvants, and the like. Preferably, the formulation will be about 5% to 75% by weight of a composition of the invention, with the remainder consisting of suitable pharmaceutical excipients. Appropriate excipients can be tailored to the particular composition and route of administration by methods well known in the art (see, e.g., REMINGTON'S PHARMACEUTICAL SCIENCES, 18TH ED., Mack Publishing Co., Easton, Pa. (1990)).

The formulations can take the form of solid, semi-solid, lyophilized power, or liquid dosage forms, such as, for example, tablets, pills, capsules, powders, solutions, suspensions, emulsions, suppositories, retention enemas, creams, ointments, lotions, aerosols or the like. In embodiments where the pharmaceutical composition takes the form of a pill, tablet or capsule, the formulation can contain, along with the biologically active composition, any of the following: a diluent such as lactose, sucrose, dicalcium phosphate, and the like; a distintegrant such as starch or derivatives thereof; a lubricant such as magnesium stearate and the like; and a binder such as starch, gum acacia, polyvinylpyrrolidone, gelatin, cellulose and derivatives thereof. Compositions can be presented in unit-dose or multi-dose sealed containers, such as ampules or vials. Doses administered to a patient should be sufficient to effect a beneficial therapeutic response in the patient over time.

In some embodiments, a sustained-release formulation can be administered to an organism or to cells in culture and can carry the desired compositions. The sustained-release composition can be administered to the tissue of an organism, for example, by injection. By "sustained-release", it is meant that the composition, preferably one encoding a transgene of interest or a therapeutic agent, is made available for uptake by surrounding tissue or cells in culture for a period of time longer than would be achieved by administration of the composition in a less viscous medium, for example, a saline solution.

The compositions, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. For delivery by inhalation, the compositions can also be delivered as dry powder (e.g., Inhale Therapeutics).

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Other methods of administration include, but are not limited to, administration using angioplastic balloons, catheters, and gel formations. Methods for angioplastic balloon, catheter and gel formation delivery are well known in the art.

Imaging Methods

One of skill in the art will understand that the compositions of the present invention can by tailored for a variety of imaging uses. In one embodiment, virtual colonoscopy can be performed using the component-based system for imaging. At present, virtual colonoscopy involves essentially infusing contrast into a colon and visualizing the images on CT, then reconstructing a 3-D image. Similar techniques could be employed for MR. However, feces, mucous, and air all serve as contrast barriers and can give an artificial surface to the colon wall reconstruction. Addition of a cellular-targeting contrast would help overcome these barriers to provide a true wall reconstruction and help avoid both false-positives and false-negatives. There are several ways that the component-based system could be applied here. Most simply, the cationic efficiency backbone could be applied with a single contrast agent (CT or MR). Thus, the cellular surface layer could be visualized and any irregularities or obstructions detailed in the image reconstruction. However, the component based system offers the additional option of adding a specific second agent. This agent could consist of a the cationic efficiency backbone, a different imaging moiety, and targeting components (for example targeting two antigens characteristic of colon cancer). The imaging moieties (from the simple to the diagnostic) could be selected so that one was CT contrast and the other MR contrast, or so that both were MR contrast with one being a T2 agent and the other a T1 agent. In this manner, the surface could be reconstructed as before, and any regions specific for a tumor antigen could be visualized and overlayed on the original reconstruction. Additionally, therapeutic agents could be incorporated into the targeted diagnostic system as well. Similar strategies could be applied to regional enteritis and ulcerative colitis (and again combined with therapy).

EXAMPLES

Example 1

This example illustrates the preparation and evaluation of a composition having a positively charged backbone, a negatively charged backbone with attached imaging moieties, and cDNA encoding a transgene. Evaluation is in vitro.

The following components are prepared:

1. a positively charged backbone composed of polylysine with $Gly_3Arg_7$ (SEQ ID NO:1) linked via the side chain amino terminus of Lys to the carboxy terminus of $Gly_3Arg_7$ (SEQ ID NO:1) at a degree of saturation of 20%. A solution is prepared of the backbone moiety at a concentration of 1.5 mg/mL in phosphate buffered saline (PBS).

2. cDNA expressing blue fluorescent protein under the control of a cytomegalovirus (CMV) promoter is prepared and used at a 0.5 mg/mL concentration in PBS.

3. a dextran- DOTA- gadolinium complex (see, Casali, et al., *Acad. Radiol.* 5:S214-S218 (1998)) is used at a 1:2 dilution in PBS.

The following mixture (a) is prepared in triplicate: 100 µL of "2" above is mixed with 60 µL of "3" above and diluted with 140 µL PBS, then vortexed for 45 seconds.

Three different tubes with the following are prepared:
(b) 400 µL "1" above, (c) 200 µL "1" above diluted with 200 µL PBS, and (d) 100 µL "1" above diluted with 300 µL PBS.

All three tubes are vortexed for 45 seconds. One tube of "a" is combined with each of tubes "b," "c," and "d" and vortexed for 90 seconds. A 200 µL portion of each of these combined mixtures is placed in a separate well (in triplicate) on a six-well cell culture plate containing HA-VSMC cells (ATCC, Rockville, Md.). Each well is pre-washed one time with dye-free, serum-free M-199 media prior to transfection. The cell/transfection agent mixtures are incubated at 37° C. in a humidified 10% $CO_2$ chamber for 4.5 hours, washed with M-199 media, then incubated with 10% FBS. Image in MR spectroscopy for initial distribution immediately. After 24 hours, repeat spectroscopy, then remove cells from plate and employ for FACS analysis for blue fluorescent protein to determine efficiency of transfection.

Example 2

This example illustrates the preparation of a composition of the invention which is an imaged tumor-specific complex carrying a cytotoxic gene.

The following components are prepared:

1. a positively charged backbone composed of polylysine with $Gly_3Arg_7$ (SEQ ID NO:1) linked via the side chain amino terminus of Lys to the carboxy terminus of $Gly_3Arg_7$ (SEQ ID NO:1) at a degree of saturation of 20%. A solution is prepared of the backbone moiety at a concentration of 1.5 mg/mL in phosphate buffered saline (PBS).

2. cDNA expressing herpes simplex virus thymidine kinase gene under the control of a cytomegalovirus (CMV) promoter is used at a 0.5 mg/mL concentration in PBS.

3. dextran-DOTA-gadolinium complex is used at a 1:2 dilution in PBS.

4. Conjugate Fab fragment specific for desired tumor antigen at a 5% saturation rate to dextran of size range and concentration in PBS selected to afford 1:2 negative charge ratio relative to component "2" above.

Prepare the following mixture (a) in triplicate: 100 µL of "2" above mixed with 60 µL of "3" above and 100 µL "4" above and diluted with 40 µL PBS and vortexed for 45 seconds. Prepare three different tubes: (b) 400 µL "1" above, (c) 200 µL "1" above diluted with 200 µL PBS, and (d) 100 µL "1" above diluted with 300 µL PBS. Vortex all three for 45 seconds. Combine one tube of "a" with "b" and vortex for 90 seconds to form mixture B. Combine one tube of "a" with "c" and vortex for 90 seconds to form mixture C. Combine one tube of "a" with "d" and vortex for 90 seconds to form mixture D. Use 200 µL of each mixture together with 200 µL of cold 30% pluronic F-127 (BASF). Inject combined solution into potential space created by excisional biopsy of putative tumor in vivo. Image in MR after implantation, after 1 day and after 3 days. Immediately after implantation, begin gancyclovir systemic administration according to FDA guidelines. This composite system provides diagnostic imaging of the desired tumor cells as well as cytotoxic therapy for these same cells. Gel (pluronic) distribution is imaged at time zero. After 24 hours, gel is degraded and contrast signal concentrates at sites of residual tumor microinvasion as well as at seeded sites along drainage pathways. Imaging of residual tumor is thus afforded. Gancyclovir activity will be concentrated in areas of HSV-TK uptake, so that targeted therapy is also afforded in this system. Monitoring of response to therapy is also afforded similarly by imaging.

Example 3

This example illustrates the use of the multi-component strategy for transfection in cell culture.

In this example a 6-well plate was used to evaluate one iteration of the component-based strategy. The positively charged backbone was assembled by conjugating -$Gly_3Arg_7$ (SEQ ID NO:1) to polylysine 150,000 via the carboxyl of the terminal glycine to the free amine of the lysine sidechain at a degree of saturation of 18% (i.e., 18 out of each 100 lysine residues is conjugated to a -$Gly_3Arg_7$ (SEQ ID NO:1)). The resultant backbone was designated NUNU-01.

The following mixtures were prepared:
1) polylysine (150,000) at a 4:1 charge ratio to a 0.5 mg/ML solution of a plasmid expressing blue fluorescent protein driven by a CMV promoter.
2) NUNU-01 at a ratio of 15:1 to a 0.5 mg/mL solution of a plasmid expressing blue fluorescent protein driven by a CMV promoter.
3) NUNU-01 at a ratio of 10:1 to a 0.5 mg/mL solution of a plasmid expressing blue fluorescent protein driven by a CMV promoter.
4) NUNU-01 at a ratio of 4:1 to a 0.5 mg/mL solution of a plasmid expressing blue fluorescent protein driven by a CMV promoter.
5) NUNU-01 at a ratio of 1.25:1 to a 0.5 mg/mL solution of a plasmid expressing blue fluorescent protein driven by a CMV promoter.
6) Superfect (Qiagen) according to the manufacturer's recommendation at a 5:1 charge ratio to a 0.5 mg/mL solution of a plasmid expressing blue fluorescent protein driven by a CMV promoter.

About 1.0 mL of each solution was added to 70% confluent HA-VSMC primary human aortic smooth muscle cells (passage 21; ATCC, Rockville, Md.) on a six well plate and grown in M-199 with 10% serum for 48 hours. Low magnification photographs (10× total) were obtained at 60 degrees, 180 degrees and 200 degrees from the top of each well using a Nikon E600 epi-fluorescence microscope with a blue fluorescent protein filter and plan apochromat lenses. Image Pro Plus 3.0 image analysis suite was employed to determine the percent of total cell area that was positive, and reported as efficiency of gene delivery. Wells were subsequently evaluated in a dye exclusion assay (viable cells exclude dye, while nonviable ones cannot), followed by solubilization in 0.4% SDS in phosphate buffered saline. Samples were evaluated in a Spectronic Genesys 5 UV/VIS spectrophotometer at 595 nm wavelength (blue) to quantitate nonviable cells as a direct measure of transfection agent toxicity.

Results for efficiencies are as follows (mean+/−Standard Error):
1) 0.163+/−0.106%
2) 10.642+/−2.195%
3) 8.797+/−3.839%
4) 15.035+/−1.098%
5) 17.574+/−6.807%
6) 1.199+/−0.573%

Runs #4 and #5 exhibit statistically significant ($P<0.05$ by one factor ANOVA repeated measures with Fisher PLSD and TUKEY-A posthoc testing) enhancement of gene delivery efficiency relative to both polylysine alone and Superfect. Mean toxicity data are as follows:
Saline—0.057 A; 1) 3.460 A; 2) 0.251 A; 3) 0.291 A; 4) 0.243 A 5) 0.297 A; and 6) 0.337 A As a result, a less toxic, more efficient gene delivery can be accomplished with a ratio of 1.25 to 4.0 of NUNU-01 to DNA.

Example 4

This example illustrates the transdermal delivery of therapeutic agents using compositions of the present invention.

Biotinylation of K and KNR:

Backbones of polylysine (K) and polylysine having attached efficiency groups (KNR) were biotinylated with sulfo-NHS esters of biotin.

Materials: Protein K and KNR, having approximate MW=112,000 were used with Sulfo-NHS-LC Biotin, MW=556 (Pierce Scientific, Rockford, Ill.).

Methods: The same method and calculations were used for K and KNR, since both have similar molecular weights. The method for KNR is detailed below.

1. Prepared stock KNR solution at concentration of 1 mg/mL ($8.9 \times 10^{-6}$ mmol/mL) in phosphate buffered saline.
2. Prepared stock solution of Sulfo-NHS-LC-Biotin at 10 mg/mL concentration in deionized water immediately prior to use. The amount of biotin reagent to add to generate a 40-fold molar excess of biotin reagent was calculated for a 1 mg/mL protein solution.

Calculation:
mol protein*40 fold molar excess=mmol of Sulfo-NHS-LC-Biotin $8.9 \times 10^{-6}$ mmol Dextran*40 fold=$3.57 \times 10^{-4}$ Mmol of Sulfo-NHS-LC-Biotin reagent to add=>$3.57 \times 10^{-4}$ mmol of Sulfo-NHS-LC-Biotin*556 MW of Sulfo-NHS-LC Biotin=1.98 mg of Sulfo-NHS-LC-Biotin reagent to add Therefore, added 200 mL of Sulfo-NHS-LC-Biotin stock solution (total of 2.0 mg) to 1.0 mL KNR stock solution.

3. Incubated the test tube containing protein and biotin reagent at room temperature for 30 minutes.
4. Added reaction mixture to a microdialyzer (molecular weight cutoff of 30 KD, Pierce, Scientific, Rockford, Ill.) and centrifuged at 4,000×g to remove unreacted biotin. Washed and re-dialyzed with 2.0 volumes of PBS. Labeled the product "KNR-B."

Biotinylation of Insulin:

Insulin was also biotinylated with sulfo-NHS esters of biotin.

Materials: Insulin, MW=5733.5 (Sigma Chemical, St Louis, Mo.) and Sulfo-NHS-LC Biotin, MW=556 (Pierce Scientific, Rockford, Ill.).

Methods:
1. Prepared stock insulin solution at concentration of 10 mg/mL ($1.74 \times 10^{-3}$ mmol/mL insulin) in phosphate buffered saline.
2. Prepared stock solution of Sulfo-NHS-LC-Biotin at 10 mg/mL concentration in deionized water immediately prior to use. Calculated amount of biotin reagent to add to generate a 12-fold molar excess of biotin reagent to a 1 mg/mL protein solution.

Calculation:
Calculated mmoles of Biotin reagent to add:
mol protein*12 fold molar excess=mmol of reagent $1.74 \times 10^{-3}$ mmol insulin*12 fold=$2.09 \times 10^{-2}$ mmol of Sulfo-NHS-LC-Biotin reagent to add=>$2.09 \times 10^{-2}$ mmol*556 MW of Sulfo-NHS-LC Biotin=11.64 mg of Sulfo-NHS-LC-Biotin reagent to add Therefore, added 1.164 mL of Sulfo-NHS-LC-Biotin stock solution (total of 11.64 mg) to 1.0 mL insulin stock solution.

3. Incubated the test tube containing insulin and biotin reagent at room temperature for 30 minutes. Labeled the product "insulin-B."

Harvesting Skin:

The backskin of an 8-week old female C57BL mouse was harvested for transdermal treatment to see whether biotinylated backbone and/or insulin get across skin.

Method:
1. After euthanizing a c57 BL6 mouse in a $CO_2$ chamber, approximately 6 cm$^2$ of dorsal skin of the mouse was harvested using a surgical scissors.
2. The skin was divided into six uniform pieces and placed each on one well of a 6-well plate.
3. Added Dulbecco's modified Eagle's medium (DMEM) to each plate well.
4. Prepared a 24 well plate for pinning the harvested skin. Placed small pieces of sponge into each well.
5. Cut the harvested skin samples into five smaller sections and placed each section on top of the sponge.
6. Pinned the edges of the harvested skin with four needles.
7. Added DMEM to each well, but was cautious not to submerge the harvest skin in the medium.
8. Incubated the plate on ice until treatments were ready to be applied.

Preparing Transdermal Treatments:
1. The following six treatments were prepared in 2 mL of Cetaphil lotion (Galderma):

| TUBES | AGENT | BIOTINYLATED BACKBONE (+/−) | PROTEIN (INSULIN): AGENT | BIOTINYLATED PROTEIN (+/−) |
|---|---|---|---|---|
| A. | KNR | + | 1:1 | − |
| B. | KNR | + | 1:3 | − |
| C. | K | + | 1:1 | − |
| D. | K | + | 1:3 | − |
| E. | K | − | 1:3 | + |
| F. | KNR | − | 1:3 | + |

2. For tube A to D, added 200 μg of KNR or K in 2 mL of Cetaphil lotion to each tube and mixed uniformly. Added 1 mL of Poly-L-Lysine (K) without biotin to each tube and mixed uniformly.
3. For tube E, added 200 μg of KNR in 2 mL of Cetaphil lotion and mixed uniformly.
4. Made a 200-fold dilution of biotinylated insulin by adding 5.11 μL in approximately 995 μL of PBS.

Calculated protein dissolved in PBS:
   KNR=$8.9 \times 10^{-9}$ mol/mL
   K=$8.9 \times 10^{-9}$ mol/mL
   Insulin=$1.74 \times 10^{-6}$ mol/mL Calculated protein in the tubes:
   KNR=$8.9 \times 10^{-10}$ mol/mL
   K=$8.9 \times 10^{-10}$ mol/mL1

5. For tubes E and F, added 33 μL of diluted biotinylated insulin solution and 70 μL of PBS and mixed uniformly.
6. For tubes A and C, added 100 μL of regular insulin and mixed uniformly.
7. For tubes B and D, added 33 μL of regular insulin and 70 μL of PBS and mixed uniformly.

Time Points of Treatments:
1. Removed the harvested skin plate from ice incubation.
2. Applied each tube to the appropriate column of pinned skin samples.
3. Transferred harvest skin to −35° C. freezer at the end of each time points of 15, 30, 60 minutes and 17 hours. Kept the harvest skin frozen overnight.
4. Took the frozen harvest skin samples and place it on ice incubation.
5. Cut the harvest skin samples that have been frozen at time points into smaller three sections.
6. Transferred one section into a tube with formaldehyde.
7. Transferred second section into an empty tube and place it into the freezer for storage.
8. Frozen third section in O.C.T. compound in liquid acetone and dry ice solution. Placed the frozen samples into the freezer for frozen sections.

Material: NeutraAvidin™ Alkaline Phosphate Conjugated (Pierce Scientific, Rockford, Ill.); Tris-HCl buffer, pH=7.2 (Pierce Scientific, Rockford, Ill.); NBT/BCIP solution (Pierce Scientific, Rockford, Ill.).

Method:
1. Added 50 μL of NeutraAvidin™ and took the volume up to 50 mL with Tris-HCl buffer.
2. Added 1 mL of NeutraAvidin™ and buffer solution to each tube of harvested skin samples.
3. Ran the tubes of harvested skin samples for 1 hour in the NeutraAvidin™ and buffer solution.
4. Added 1 mL of NBT/BCIP each to new empty tubes and labeled each tube.
5. Removed the skin from NeutraAvidin™ and buffer solution. Rinsed the skin in PBS four times and placed it into appropriate NBT/BCIP tubes.
6. Ran the tubes of harvested skin samples for 1 hour in the NBT/BCIP solution.
7. Rinsed skin in 1 mL of cold PBS again.
8. Stored the harvested skin samples in the labeled tubes.
9. Bisected skin samples and photographed bisected face.

Results:

| Formulation | Timepoint | Figure | Notes |
|---|---|---|---|
| A | 15 minutes | 3 | A1 - high level delivery of KNR backbone across all layers |
| A | 17 hours | 4 | A4 - high level delivery of KNR backbone across all layers |
| C | 15 minutes | 5 | C1 - passive delivery of K backbone at follicles and outer layer of epidermis |
| C | 17 hours | 6 | C4 - very low level delivery of K backbone |
| E | 15 minutes | 7 | E1 - very low level delivery of therapeutic factor by K |
| E | 17 hours | 8 | E4 - very low level delivery of therapeutic factor by K |
| F | 15 minutes | 9 | F1 - high level delivery of therapeutic factor across all layers by KNR |
| F | 17 hours | 10 | F4 - high level delivery of therapeutic factor across all layers by KNR |

Figure 7:
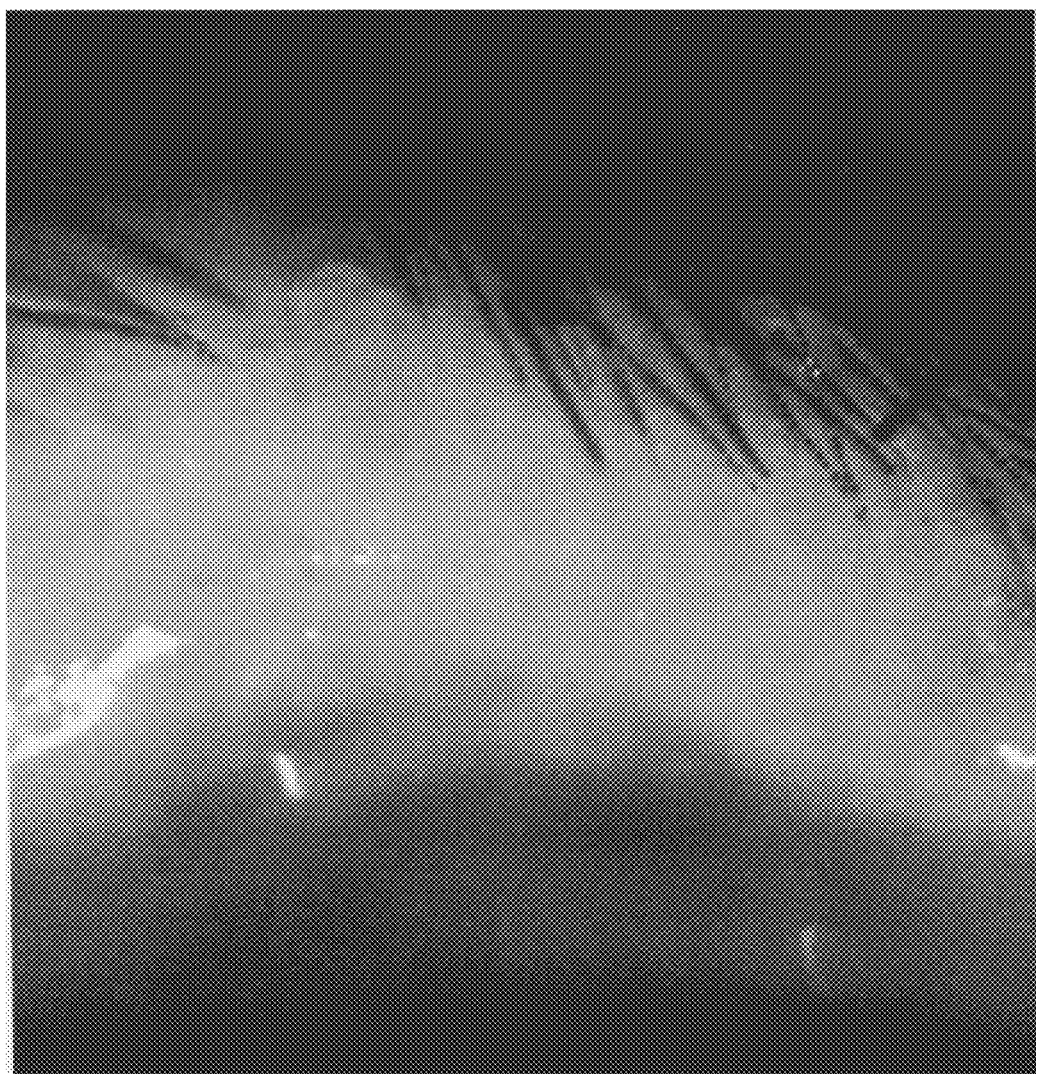
Figure 8:
Figure 9:
Figure 10:

FIGS. 3-10 depict representative photomicrographs of results obtained after 15 minutes (FIGS. 3, 5, 7, 9) and 17 hours (FIGS. 4, 6, 8, 10) delivery of formulation A (FIGS. 3 and 4), formulation C (FIGS. 5 and 6), formulation E (FIGS. 7 and 8), and formulation F (FIGS. 9 and 10). Control groups receiving complexes with K as the positively charged backbone exhibit low-level passive transfer of backbone primarily to follicles (FIGS. 5 and 6), but virtually no delivery of therapeutic agent (FIGS. 7 and 8). In contrast, groups treated with complexes containing KNR exhibit high-level delivery of both backbone (FIGS. 3 and 4) and therapeutic agent (FIGS. 9 and 10) to all levels of the epidermis and dermis. Thus, the formulation provided in this example allows efficient transdermal delivery of a therapeutic agent.

Example 5

This example illustrates the targeted delivery of a composition using attached F(ab)$_2$ fragments.

General:

An IgG antibody was cleaved to generate an F(ab)$_2$ fragment, then purified to remove Fc and intact IgG. The F(ab)$_2$ fragment was then condensed with an aldehyde activated (oxidized) dextran. Excess aldehydes were quenched with tris and free hydroxyls were phosphorylated to generate a highly negatively charged dextran-phosphate with F(ab)$_2$ fragments covalently bonded (collectively referred to as "targeting component"). A self-assembling complex was then formed between this targeting component, insulin, and the positively charged backbone having an efficiency component ("KNR"). The ability of the self-assembled complex to enhance delivery of the complex to cells bearing the target antigen was then evaluated.

F(ab)$_2$ Cleavage:

F(ab)$_2$ fragments recognizing smooth muscle cells were generated by an immobilized pepsin (Pierce Chemical, Rockford, Ill.) digest of IgG for smooth muscle α-actin (clone 1A9, DAKO, Carpinteria, Calif.).

Method:
1. Dialyzed clone 1A9 at 1 mg/mL against a 20 mM sodium acetate buffer at pH 4.5.
2. Immobilized Pepsin was supplied as a 50% (v/v) aqueous slurry containing 50% glycerol in 0.1 M sodium acetate, pH 4.5, plus 0.05% sodium azide. Mixed Pepsin gel-glycerol-water slurry by inversion.
3. Added 0.25 mL of 50% slurry of Immobilized Pepsin to a glass test tube (0.125 mL of Immobilized Pepsin gel).
4. Added 4.0 mL of 20 mM sodium acetate (pH 4.0) in deionized water ("digestion buffer"). Mixed well by inversion. Separated gel from buffer using a serum separator or centrifugation at approximately 1000×g for five minutes. Discarded buffer and repeated this wash procedure with another 4.0 mL of buffer.
5. Resuspended the Immobilized Pepsin in 0.5 mL of digestion buffer.
6. Generation of Fragments: Added 1.0 mL of dialyzed 1A9 IgG to the tube containing Immobilized Pepsin. Incubated the tube in a shaking water bath at 37° C. at high speed for four hours. Maintained constant mixing of gel during the incubation.
7. Added 1.5 mL of 10 mM Tris-HCl, pH 7.5 to test tube. Separated the solubilized F(ab')$_2$ and Fc and undigested IgG from the Immobilized Pepsin gel using a serum separator tube. Centrifuged at 1000×g for five minutes and removed the supernatant containing the fragments.

F(ab)$_2$ Purification:
Separation of F(ab)$_2$ fragments from undigested IgG and Fc fragments was carried out using an Immobilized Protein A Column.
Materials: Protein Sample made of Pepsin+Tris-HCl; Buffer A (0.2 M NaH$_2$PO$_4$ (2.4 g used), 0.15 M NaCl (8.8 g used), QS adjusted volume to 1 liter with deionized H$_2$O and tested pH for 8.0); Buffer B (0.2 M Na$_2$HPO$_4$ (0.676 g), 0.1 M Citric Acid (22.5 ml), deionized H$_2$O (46.3 ml), adjusted pH to 4.5).
Method: (Note: Use of Buffer A).
1. Packed micropipet with cotton uniformly as possible.
2. Made a 1:1 suspension of resin in Buffer A. (Added 1000 µL of Buffer A in resin. Poured 1 mL suspension into column. Allowed column to flow as it is settling. When it was settled, the column was washed with 10 mL of Buffer A).
3. Slowly added protein sample to column.
4. Eluted F(ab)$_2$ fragment with 12 mL of Buffer A. F(ab)$_2$ eluate total volume (including column load) was thus 14.4 mL.
5. Stripped unreacted IgG and Fc fragments from column with 1.5 mL of Buffer B.
6. Measured and recorded absorbance using a spectrophotometer (Spectronic Genesys 5) to confirm protein in eluates. The following are the recorded spectronic values:

| COLUMN FRACTIONS | VALUES |
| --- | --- |
| H$_2$O | −0.032 |
| H$_2$O and A | +0.009 |
| H$_2$O and B | +0.012 |

F(ab)$_2$ Concentration:
The F(ab)$_2$ eluate was purified and concentrated using Tricholoroacetic Acid (TCA) Protein Precipitation.
Method:
1. Added an equal volume of 20% TCA (w/v, in deionized water, Sigma Chemical, St Louis, Mo.) to the F(ab)$_2$ column eluate.
2. Incubated sample for 30 minutes on ice.
3. Centrifuged sample in microcentrifuge at 4000×g for 15 minutes at 4° C.
4. Carefully removed all of the supernatant.
5. Added 300 µL of cold acetone to each tube and centrifuged again at 4000×g for 5 minutes at 4° C.
6. Removed the supernatant and allowed the F(ab)$_2$ to dry.
7. Suspended F(ab)$_2$ protein pellet in 1.0 mL of phosphate buffered saline.

Coupling of F(ab)$_2$ to Aldehyde-activated Dextran:
Materials: Aldehyde-Activated Dextran Coupling Kit (Pierce, Rockford, Ill.). [Note: Aldehyde-activated dextran can also be generated through periodate treatment of dextran.]
Methods:
1. Brought Aldehyde-Activated Dextran Coupling Kit to room temperature.
2. Prepared 0.5 mL of a 64 mg/mL stock solution of sodium cyanoborohydride in phosphate buffered saline (32 mg in 0.5 mL).
3. Prepared 1.0 mL of a 5 mg/mL Aldehyde-Activated Dextran stock solution in phosphate buffered saline.
4. Added 1.0 mL of purified, concentrated F(ab)$_2$ from above to 1.0 mL of Aldehyde-Activated Dextran stock solution.
5. Added 0.2 mL of sodium cyanoborohydride stock solution to the aldehyde-F(ab)$_2$ mixture. Mixed by vortex and incubated overnight in the dark at room temperature.
6. After overnight incubation, blocked any remaining aldehyde groups by adding 0.5 mL of 1.0 M Tris-HCl, pH 7.2 to the reaction mixture. Incubated the solution at room temperature for 1 hour.
7. Product is labeled "F(ab)$_2$(aact)-d-t" with total volume of 2.7 mL.
8. An identical procedure was carried out using 1.0 mL deionized water in place of F(ab)$_2$ mixture. The product was labeled "d-t" and represents a control that does not target a specific antigen.

Phosphorylation of F(ab)$_2$(act)-d-t:
1. Prepared stock solution of 50 mg/mL polyphosphoric acid (Acros Organics, Pittsburgh, Pa.) in deionized water.
2. Added 100 µL of polyphosphoric acid stock solution to 1.0 mL of F(ab)$_2$(aact)-d-t, and incubated for 60 minutes at room temperature.
3. Added reaction mixture to a microdialyzer (molecular weight cutoff of 30 KD, Pierce, Scientific, Rockford, Ill.) and centrifuged at 4,000×g to remove unreacted polyphosphoric acid. Washed and re-dialyzed with 2.0 volumes of PBS pH 7.4. Product was labeled "F(ab)$_2$(aact)-d-t-p" and represents a negatively charged polymer with an attached $F(ab)_2$ fragement to afford targeting.
4. An identical procedure was carried out using 1.0 mL of d-t in place of $F(ab)_2$(aact)-d-t. The product was labeled "d-t-p" and represents a negatively charged polymer control that does not target a specific antigen.

Targeting of Therapeutic Complex Delivery to Cells Bearing a Particular Antigen (Smooth Muscle Cell α-actin):

1. Male New Zealand White rabbits (3.0-3.5 kg) were used in accordance to NIH and institutional guidelines (n=3 animals). Under general anesthesia (ketamine/xylazine induction and halothane maintenance), right common femoral artery was isolated and adventitia circumferentially exposed. A 2 mm×2 cm SAVVY angioplasty balloon (Cordis, Miami, Fla.) was introduced via arteriotomy in the superficial femoral artery and advanced into the common femoral artery. The balloon was inflated to 6 atm in two 1-minute cycles then withdrawn.

2. 28 days after mechanical dilation, arteries were perfusion-fixed and harvested. Harvested arteries (approximately 1.5 cm in length) were post-fixed in 10% neutral buffered formalin for 12-16 hours and divided into three equal segments prior to paraffin embedding. Serial (5 μm) cross-sections were obtained from the proximal (cranial) face of each segment.

3. Deparaffinized and rehydrated sections (n=9 per group). Blocked nonspecific binding sites with BLOTTO (Pierce Scientific, Rockford, Ill.), and rinsed with phosphate buffered saline.

4. Labeled treatments "1p" and "2p" to correspond to the following treatment compositions: [NOTE: "KNR-B" prepared as above]

|  | Efficiency agent (E) | Targeting agent (T) | Protein (P) | Ratio E:T:P |
|---|---|---|---|---|
| 1p | KNR - B | F(ab)2(aact)-d-t-p | Insulin | 2:1:1 |
| 2p | KNR - B | d-t-p | Insulin | 2:1:1 |

Mixed 180 μL of phosphate buffered saline, 5 μL of protein therapeutic and 5 μL targeting agent (both negative net surface charge) in a microfuge tube and vortexed for 15 seconds. Added 10 μL of targeting agent (positively charged) and immediately vortexed for 60 seconds. Using capillary gap methods, incubated 9 sections each with either 1p or 2p at room temperature overnight.

5. Rinsed slides and incubated overnight in 1:100 dilution of Neutravidin-Alkaline phosphatase (Pierce Scientific, Rockford, Ill.).

6. Rinsed slides and incubated in NBT/BCIP (Pierce Scientific, Rockford, Ill.; substrate for alkaline phosphatase) for 15 minutes. Rinsed with saline and photographed.

Figure 11:
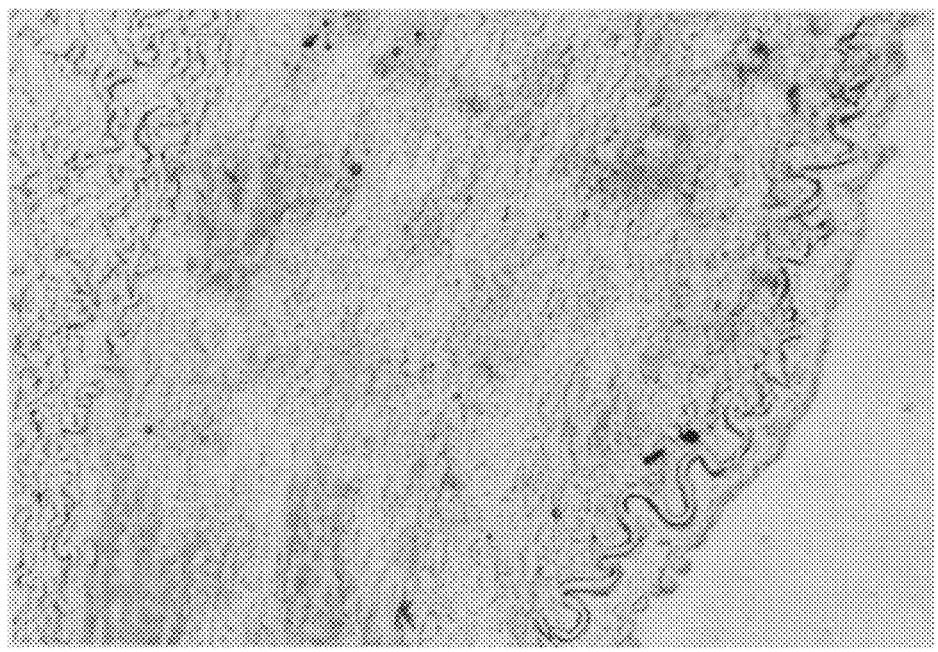
FIGS. 11-12 provide photographs depicting targeting of a therapeutic formulation as described in Example 5.
Figure 12:
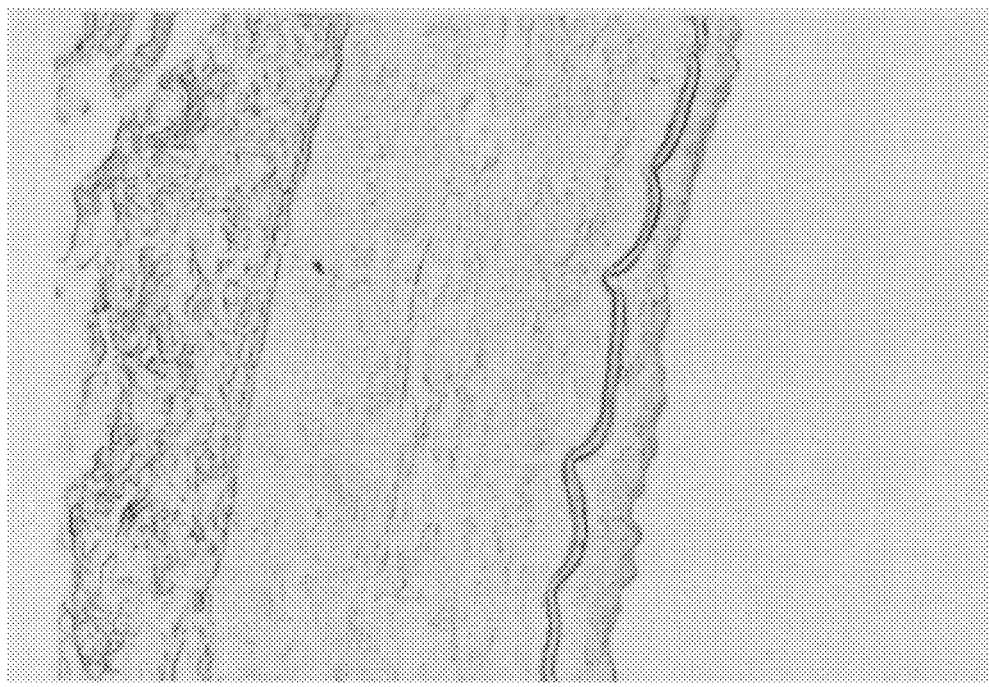

As shown in FIG. 11, sections from 1P treatments reveal an increase in positive (blue-purple) staining in the media of the cross sections (primarily composed of smooth muscle cells bearing high levels of α-actin) relative to 2P sections which show most intense staining in the adventitia, and reveal no specific targeting enhancement for smooth muscle cells, as depicted in FIG. 12. Thus, complexes bearing $F(ab)_2$(aact)-d-t-p exhibit relative increases in specific delivery to smooth muscle cells, and delivery of therapeutic agents can thus have targeted enhancements in efficiencies for cells bearing particular antigens.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising a non-covalent association complex of:
   a positively charged backbone covalently attached to a plurality of amino acid sequences, wherein said amino acid sequences are selected from the group consisting of $(gly)_p$-RGRDDRRQRRR-$(gly)_q$ (SEQ ID NO:19), and $(gly)_p$-YGRKKRRQRRR-$(gly)_q$ (SEQ ID NO: 20) wherein p and q are each independently an integer of from 0 to 20;
   a negatively charged backbone having a plurality of attached targeting agents;
   a negatively charged backbone having a plurality of attached biological agents, wherein each of said biological agents is a therapeutic agent or a cosmeceutical agent selected from the group consisting of VEGF, botulinum toxin, EGF, TGF-b1, insulin, a blocker of VEGF, and antibodies to VEGF; and
   wherein said non-covalent association complex carries a net positive charge.

2. The composition according to claim 1, wherein said amino acid sequences have the formula $(gly)_p$-RGRD-DRRQRRR-$(gly)_q$ (SEQ ID NO:19), wherein p and q are each independently an integer from 0 to 20, and wherein each of said amino acid sequences is attached to said positively charged backbone via the C-terminus or the N-terminus of said each amino acid sequence.

3. The composition in accordance with claim 2, wherein the subscripts p and q are each independently integers of from 0 to 8.

4. The composition in accordance with claim 3, wherein the subscripts p and q are each independently integers of from 2 to 5.

5. The composition according to claim 2, wherein therapeutic agent is botulinum toxin.

6. The composition according to claim 1, wherein the biological agent is a therapeutic agent.

* * * * *

UNITED STATES PATENT AND TRADEMARK OFFICE
CERTIFICATE OF CORRECTION

| | | |
|---|---|---|
| PATENT NO. | : 7,807,780 B2 | Page 1 of 1 |
| APPLICATION NO. | : 09/910432 | |
| DATED | : October 5, 2010 | |
| INVENTOR(S) | : Jacob Waugh et al. | |

It is certified that error appears in the above-identified patent and that said Letters Patent is hereby corrected as shown below:

Column 1, lines 7-9, the text reading: "This application claims priority to provisional application Ser. No. 60/220,244, filed Jul. 21, 2001, the contents of which are incorporated herein by reference."

should read: -- This application claims priority to provisional application Ser. No. 60/220,244, filed Jul. 21, 2000, the contents of which are incorporated herein by reference. --

Signed and Sealed this
Twenty-eighth Day of June, 2011

David J. Kappos
*Director of the United States Patent and Trademark Office*

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone (Gly-3Arg-7, G3R7)

<400> SEQUENCE: 1

Gly Gly Gly Arg Arg Arg Arg Arg Arg Arg
 1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(3)
<223> OTHER INFORMATION: Gly at positions 1-3 may be present or absent

<400> SEQUENCE: 2

Gly Gly Gly Gly Gly Arg Arg Arg Arg Arg Arg Arg
 1               5                   10

<210> SEQ ID NO 3
<211> LENGTH: 14
```

```
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(3)
<223> OTHER INFORMATION: Gly at positions 1-3 may be present or absent

<400> SEQUENCE: 3

Gly Gly Gly Gly Gly Arg Arg Arg Arg Arg Arg Arg Arg Arg
 1               5                  10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(3)
<223> OTHER INFORMATION: Gly at positions 1-3 may be present or absent

<400> SEQUENCE: 4

Gly Gly Gly Gly Gly Arg Arg Arg Arg Arg Arg Arg Arg Arg Arg Arg
 1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(3)
<223> OTHER INFORMATION: Gly at positions 1-3 may be present or absent

<400> SEQUENCE: 5

Gly Gly Gly Gly Gly Arg Arg Arg Arg Arg Arg Arg Arg Arg Arg Arg
 1               5                  10                  15

Arg Arg

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(3)
<223> OTHER INFORMATION: Gly at positions 1-3 may be present or absent

<400> SEQUENCE: 6

Gly Gly Gly Gly Gly Arg Arg Arg Arg Arg Arg Arg Arg Arg Arg Arg
 1               5                  10                  15

Arg Arg Arg Arg
            20
```

```
<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(3)
<223> OTHER INFORMATION: Gly at positions 1-3 may be present or absent

<400> SEQUENCE: 7

Gly Gly Gly Gly Gly Arg Arg Arg Arg Arg Arg Arg Arg Arg Arg
 1               5                  10                  15

Arg Arg Arg Arg Arg Arg
            20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 8

Gly Gly Gly Gly Gly Gly Gly Gly Gly Gly Gly Gly Gly Gly Gly
 1               5                  10                  15

Gly Gly Gly Gly Arg Arg Arg Arg Arg
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 9

Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent
```

```
<400> SEQUENCE: 10

Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg
            20                  25

<210> SEQ ID NO 11
<211> LENGTH: 31
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 11

Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg Arg Arg
            20                  25                  30

<210> SEQ ID NO 12
<211> LENGTH: 33
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 12

Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg Arg Arg Arg
            20                  25                  30

Arg

<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 13

Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg Arg Arg Arg
            20                  25                  30

Arg Arg Arg
        35
```

```
<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 14

Gly Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg Arg Arg Arg
            20                  25                  30

Arg Arg Arg Arg Arg
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 15

Gly Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg Arg Arg Arg
            20                  25                  30

Arg Arg Arg Arg Arg Arg Arg
        35

<210> SEQ ID NO 16
<211> LENGTH: 41
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 16

Gly Gly Gly Gly Gly Gly Gly Gly Gly Gly Gly Gly Gly Gly Gly Gly
 1               5                  10                  15

Gly Gly Gly Gly Arg Arg Arg Arg Arg Arg Arg Arg Arg Arg Arg Arg
            20                  25                  30

Arg Arg Arg Arg Arg Arg Arg Arg Arg
        35                  40

<210> SEQ ID NO 17
<211> LENGTH: 43
<212> TYPE: PRT
```

```
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 17

Gly Gly Gly Gly Gly Gly Gly Gly Gly Gly Gly Gly Gly Gly Gly Gly
  1               5                  10                  15

Gly Gly Gly Gly Arg Arg Arg Arg Arg Arg Arg Arg Arg Arg Arg
             20                  25                  30

Arg Arg Arg Arg Arg Arg Arg Arg Arg Arg Arg
         35                  40

<210> SEQ ID NO 18
<211> LENGTH: 45
<212> TYPE: PRT
<213> ORGANISM: Artificial Sequence
<220> FEATURE:
<223> OTHER INFORMATION: Description of Artificial Sequence:positively
      charged branching group (efficiency group)
      attached to solid backbone
<220> FEATURE:
<221> NAME/KEY: MOD_RES
<222> LOCATION: (1)..(20)
<223> OTHER INFORMATION: Gly at positions 1-20 may be present or absent

<400> SEQUENCE: 18

Gly Gly Gly Gly Gly Gly Gly Gly Gly Gly Gly Gly Gly Gly Gly Gly
  1               5                  10                  15

Gly Gly Gly Gly Arg Arg Arg Arg Arg Arg Arg Arg Arg Arg Arg Arg
             20                  25                  30

Arg Arg Arg Arg Arg Arg Arg Arg Arg Arg Arg Arg Arg
         35                  40                  45

<210> SEQ ID NO 19
<211> LENGTH: 51
<212> TYPE: PRT
<213> ORGANISM: Artificial Sequence
<220> FEATURE:
<223> OTHER INFORMATION: Description of Artificial Sequence:positively
      charged HIV-TAT fragment branching group
      (efficiency group) attached to solid backbone
<220> FEATURE:
<221> NAME/KEY: MOD_RES
<222> LOCATION: (1)..(20)
<223> OTHER INFORMATION: Gly at positions 1-20 may be present or absent
<220> FEATURE:
<221> NAME/KEY: MOD_RES
<222> LOCATION: (32)..(51)
<223> OTHER INFORMATION: Gly at positions 32-51 may be present or absent

<400> SEQUENCE: 19

Gly Gly Gly Gly Gly Gly Gly Gly Gly Gly Gly Gly Gly Gly Gly Gly
  1               5                  10                  15

Gly Gly Gly Gly Arg Gly Arg Asp Asp Arg Arg Gln Arg Arg Gly
             20                  25                  30

Gly Gly Gly Gly Gly Gly Gly Gly Gly Gly Gly Gly Gly Gly Gly
         35                  40                  45

Gly Gly Gly
     50
```

```
<210> SEQ ID NO 20
<211> LENGTH: 51
<212> TYPE: PRT
<213> ORGANISM: Artificial Sequence
<220> FEATURE:
<223> OTHER INFORMATION: Description of Artificial Sequence:positively
      charged HIV-TAT fragment branching group
      (efficiency group) attached to solid backbone
<220> FEATURE:
<221> NAME/KEY: MOD_RES
<222> LOCATION: (1)..(20)
<223> OTHER INFORMATION: Gly at positions 1-20 may be present or absent
<220> FEATURE:
<221> NAME/KEY: MOD_RES
<222> LOCATION: (32)..(51)
<223> OTHER INFORMATION: Gly at positions 32-51 may be present or absent

<400> SEQUENCE: 20

Gly Gly Gly Gly Gly Gly Gly Gly Gly Gly Gly Gly Gly Gly Gly Gly
 1               5                  10                  15

Gly Gly Gly Gly Tyr Gly Arg Lys Lys Arg Arg Gln Arg Arg Arg Gly
            20                  25                  30

Gly Gly Gly Gly Gly Gly Gly Gly Gly Gly Gly Gly Gly Gly Gly
        35                  40                  45

Gly Gly Gly
    50
```